United States Patent [19]
Carroll et al.

[11] Patent Number: 5,582,994
[45] Date of Patent: Dec. 10, 1996

[54] AMINOPSORALEN COMPOUNDS FOR USE IN DECONTAMINATING CLINICAL SAMPLES

[75] Inventors: Peter G. Carroll, Walnut Creek; Stephen T. Isaacs, Orinda; George D. Cimino, Richmond, all of Calif.

[73] Assignee: Steritech, Inc., Concord, Calif.

[21] Appl. No.: 461,505

[22] Filed: Jun. 5, 1995

Related U.S. Application Data

[62] Division of Ser. No. 253,619, Jun. 3, 1994, which is a continuation of Ser. No. 32,490, Mar. 17, 1993, which is a continuation-in-part of Ser. No. 428,494, Oct. 26, 1989, Pat. No. 5,221,608.

[51] Int. Cl.$^6$ .............................. C12Q 1/68; C12Q 1/70; C12P 19/34; C07H 19/04
[52] U.S. Cl. .................. 435/6; 435/5; 435/91.1; 435/91.2; 536/26.6
[58] Field of Search ................ 435/5, 6, 91.2, 435/91.1; 536/26.6

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 546/270 |
| 4,196,281 | 4/1980 | Hearst et al. | 536/28 |
| 4,294,822 | 10/1981 | Kaufman | 424/59 |
| 4,370,344 | 1/1983 | Kaufman | 424/279 |
| 4,727,027 | 2/1988 | Wiesehahn et al. | 435/173 |
| 4,748,120 | 5/1988 | Wiesehahn | 435/173 |

OTHER PUBLICATIONS

G. D. Cimino, et al., "Psoralens as Photoactive Probes of Nucleic Acid Structure and Function: Organic Chemistry, Photochemistry, and Biochemistry," Ann. Rev. Biochem. 54:115 (1985).

Hearst et al., "The reaction of the psoralens with deoxyribonucleic acid," Quart. Rev. Biophys. 17:1 (1984).

S. T. Isaacs et al., "Synthesis and Characterization of New Psoralen Derivatives with Superior Photoreactivity with DNA and RNA," Biochemistry 16:1058 (1977).

S. T. Isaacs et al., "A Photochemical Characterization of Reactions of Psoralen Derivatives with DNA," Trends in Photobiology (Plenum) pp. 279–294 (1982).

J. Tessman et al., "Photochemistry of the Furan–Side 8–Methoxypsoralen–Thymidine Monoadduct Inside the DNA Helix. Conversion to Diadduct and to Pyrone–Side Monoadduct," Biochem. 24:1669 (1985).

H. J. Alter et al., "Photochemical Decontamination of Blood Components Containing Hepatitis B and non–A, Non–B Virus," The Lancet pp. 1446–1450 (Dec. 24/31, 1988).

L. Lin, et al., "Use of 8–Methoxypsoralen and Long–Wavelength Ultraviolet Radiation for Decontamination of Platelet Concentrates," Blood 74:517 (1989).

P. Morel et al., "Photochemical Inactivation of Viruses and Bacteriophage in Plasma and Plasma Fractions," Blood Cells 18:27 (1992).

Hyde and Hearst, "Binding of Psoralen Derivatives to DNA and Chromatin: Influence of the Ionic Environment on Dark Binding and Photoreactivity," Biochemistry 17:1251 (1978).

Thompson et al., "Determination of the Secondary Structure of *Drosphila Melanogaster* 5 S RNA by Hydroxymethyltrimethylpsoralen Crosslinking," J. Mol. Biol. 147:417 (1981).

(List continued on next page.)

*Primary Examiner*—Stephanie W. Zitomer
*Assistant Examiner*—Dianne Rees
*Attorney, Agent, or Firm*—Peter G. Carroll; Kathryn P. Wilke

[57] ABSTRACT

The present invention contemplates methods of decontaminating human fluids prior to processing in the clinical laboratory. The techniques handle large volumes of human serum without impairing the testing results. Novel compounds for photodecontaminating biological material are also contemplated which are compatible with clinical testing, in that they do not interfere with serum analytes.

6 Claims, 25 Drawing Sheets

OTHER PUBLICATIONS

Thompson et al., "Dependence of 4'-(Hydroxymethyl)-4,5',8-trimethylpsoralen Photoaddition on the Conformation of Ribonucleic Acid," Biochemistry 21:1363 (1982).

Bender, et al., "Psoralen Synthesis. Improvements in Furano Ring Formation. Application to the Synthesis of 4,5',8-Trimethylpsoralen," J. Org. Chem. 44:2176 (1979).

Hansen et al. J. Med. Chem. 28:1001–1010 1985.

Bender, et al., "Synthesis and Derivitization of 8-Acetylpsoralens. Acetyl Migrations during Claisen Rearrangement," J. Org. Chem. 48:2709 (1983).

Hanson, C. V., et al., "Application of a Rapid Microplaque Assay for Determination of Human Immunodeficiency Virus Neutralizing Antibody Titers," J. Clin. Micro 28:2030 (1990).

Lee, et al., "Interaction of psoralen-derivatized oligodeoxyribonucleoside methylphosphonates with synthetic DNA containing a promoter for T7 RNA polymerase," Nuc. Acids. Res. 16 (1988) pp. 10681–10696.

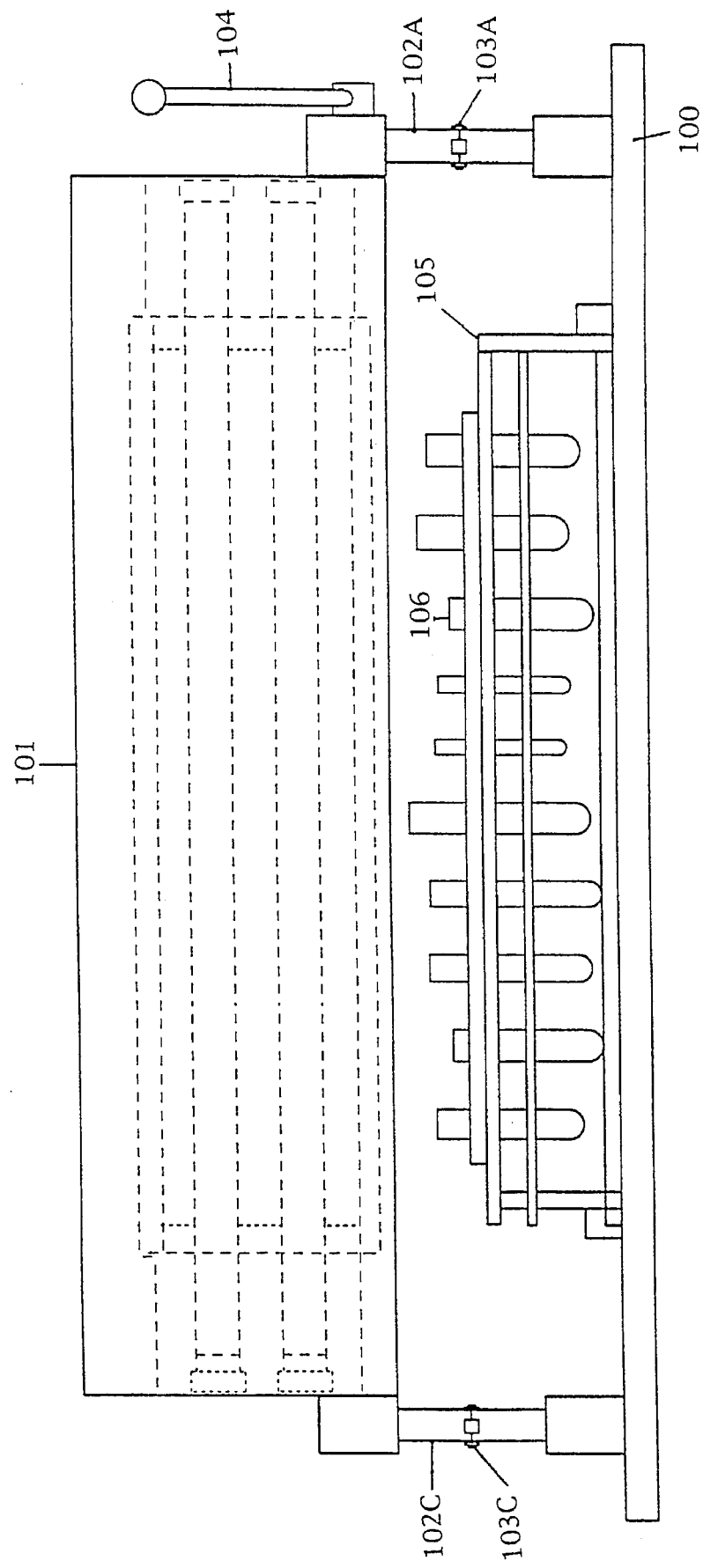

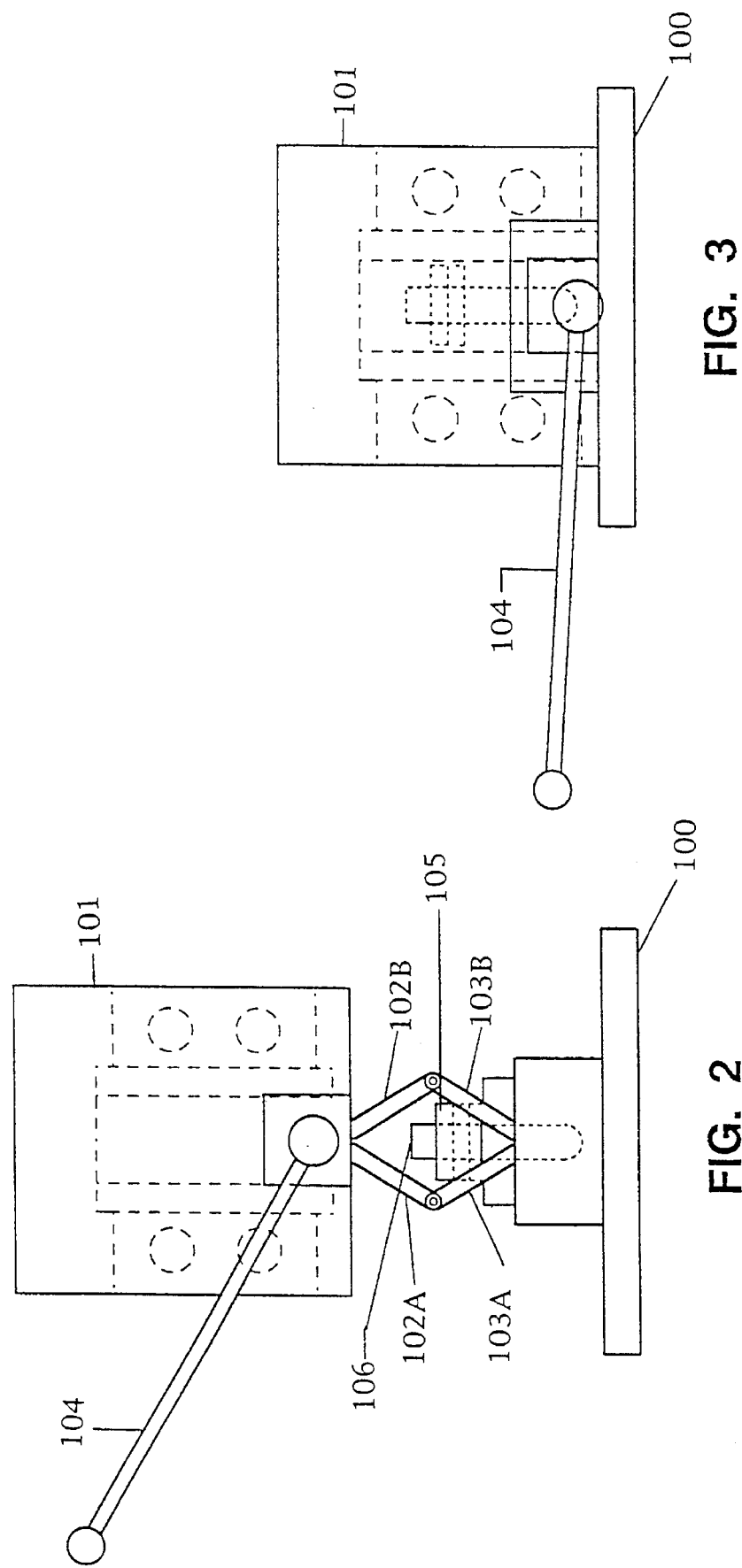

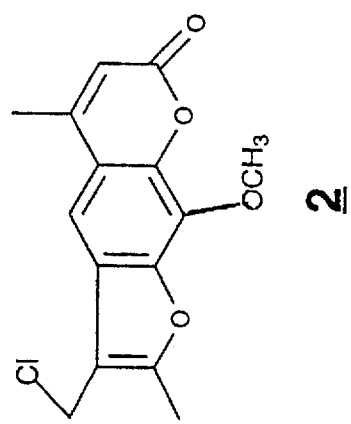
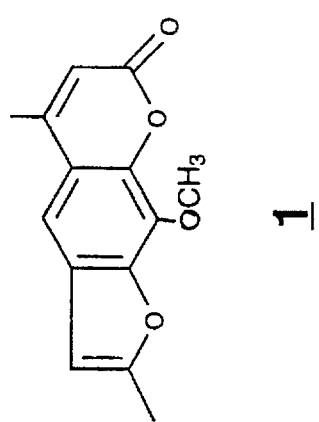
Figure 24

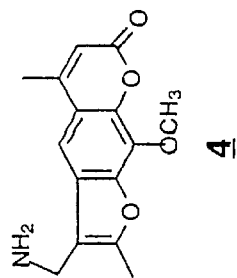
4
↑ $NH_2NH_2$
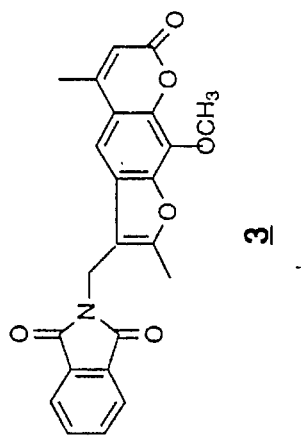
3
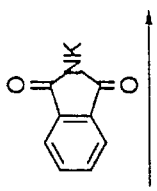
↑
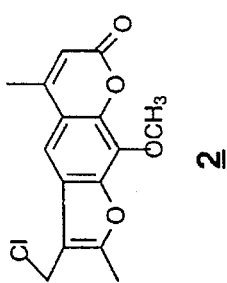
2
FIG. 25

AMINOPSORALEN COMPOUNDS FOR USE IN DECONTAMINATING CLINICAL SAMPLES

This application is a divisional application of application Ser. No. 08/253,619, filed on Jun. 3, 1994, which is a file wrapper continuation of application Ser. No. 08/032,490 filed on Mar. 17, 1993, which is a continuation in part of U.S. application Serial No. 07/428,494, filed Oct. 26, 1989, U.S. Pat No. 5,221,608.

FIELD OF THE INVENTION

The invention generally relates to the inactivation of contaminants in material intended for in vitro use, and in particular the inactivation of pathogens in human fluids prior to clinical testing.

BACKGROUND

The status of hospital patients is routinely monitored by obtaining and testing human fluids (blood, urine, spinal fluid, etc.). Testing is typically performed at a centralized location, such as a clinical laboratory.

A great volume of human fluids, and in particular, human serum, is handled daily by hospital clinical chemistry laboratories. Typically, each admitted patient has at least a tube of blood collected every day by a phlebotomist.

In a clinical laboratory, these blood samples are processed by first centrifuging the unopened tube to separate the cells from the serum or plasma. Thereafter, the tube is opened by removing the rubber stopper by hand. To maintain the separation, plastic inserts can be manually pushed down into the serum to a level just above the packed cells.

The tubes are placed in a standard test tube rack and delivered to a technologist for automated analysis. At this point, the technologist running the machine pipettes serum from the top of tube into a small sample cup. The sample cup is then placed on the instrument and processed.

This intensive handling of potentially infectious human fluids is not without health risk. The Occupational Safety and Health Administration (OSHA) estimates that over five million health workers, including hospital laboratory workers, are exposed to bloodborne-pathogen infections in the work place annually. The pathogen responsible for the overwhelming majority of infections is the hepatitis B virus (HBV). The Center for Disease Control (CDC) estimates there are twelve thousand cases of HBV infection among health workers each year. Of these cases, over five hundred require hospitalization and approximately two hundred and fifty of these patients die (i.e. from fulminant hepatitis, cirrhosis or liver cancer). See *Guidelines for Prevention of Transmission of HIV and HBV to Health-Care and Public Safety Workers*, CDC (February 1989). Most full time laboratory employees contract hepatitis at least once during their career. Indeed, up to one third of all health care workers show serological evidence of a previous HBV infection. Id.

Following the recognition of the Acquired Immunodeficiency Syndrome (AIDS), clinical laboratories have moved away from using plastic inserts to maintain the separation of cells from serum. A "gel" is now available that is in the empty tube at the time the blood is drawn. When the tube is centrifuged the cells go below the gel while the serum remains above. While the separation can be maintained in this manner without as much sample handling, this does not reduce the handling of the technologist at the point of analysis. Technologists who come into contact with the fluids from AIDS patients must be aware that infectious virus can persist in a liquid or dried state for prolonged periods of time, possibly even at elevated temperatures. Resnick et al., JAMA 255:1887 (1986).

Preventative measures such as gloves and eye-wear are not complete solutions to the problem. Accidents in the laboratory or clinic typically involve exposure over a larger portion of the body and disease can be transmitted through the skin and mucous membranes. Morbidity and Mortality Weekly Report 36:285 (1987).

Clearly, there remains a need for a more adequate solution to bloodborne-pathogen infections in the work place. Such a solution should serve as a protection against a wide range of pathogens. Furthermore, the mechanics of the solution should not unduly interfere with laboratory operations.

SUMMARY OF THE INVENTION

The present invention relates to methods of inactivating contaminants in material intended for in vitro use. In particular the present invention relates to the inactivation of pathogens in human fluids prior to clinical testing. In accordance with the present invention, a nucleic acid binding compound is selectively employed to treat contamination by nucleic acid-containing microorganisms, including pathogenic viruses. In one embodiment, the present invention contemplates a method of decontamination, comprising: a) providing, in any order, i) an aminopsoralen; ii) means for activating said aminopsoralen, iii) a biological fluid intended for in vitro testing suspected of being contaminated with one or more pathogens; b) adding said aminopsoralen to said fluid; and c) activating said aminopsoralen, so that said nucleic acid binding compound binds covalently to the nucleic acid of said pathogens.

The method of the present invention is particularly useful where the pathogens are bacteria, fungi, mycoplasma, protozoa and viruses. The present invention is employed with success with human serum and human plasma. Preferably, the intensity of light received by the human fluid is less than 20 mW/cm$^2$ and the human fluid is exposed to this intensity for less than thirty minutes.

In another embodiment, the present invention contemplates a method of treating biological material intended for in vitro clinical testing, comprising: a) providing, in any order, i) a container containing one or more aminopsoralens; ii) a photoactivation device; and iii) material intended for in vitro clinical testing suspected of being contaminated with pathogens; b) adding the material to the container; c) photoactivating the aminopsoralens, so that the aminopsoralens bind covalently to the nucleic acid of the pathogens; d) testing the material for the presence of serum analytes.

Preferably, the photoactivation device comprises filters providing wavelength cutoffs at 320 nm, below which no irradiation is transmitted, and at 360 nm, above which no irradiation is transmitted. In one embodiment, the material comprises blood.

It is not intended that the present invention be limited to particular aminopsoralens. In one embodiment, the present invention contemplates the use of 4'-aminomethyl-4,5'-trimethylpsoralen, 4'-aminomethyl-4,5'-dimethyl-8-methoxypsoralen, radiolabelled 4'-aminomethyl-4,5'-dimethyl-8-methoxypsoralen or biotinylated aminopsoralen. In a preferred embodiment the activating means comprises a photoactivation device.

It is also not intended that the invention be limited by the type of container (tube, specimen cup, etc.) or the condition of the container (opened, closed, labelled, unlabelled etc.). It is preferred however that the container be such that it is an ultraviolet light transparent container. In one embodiment, the container is a glass vacuum tube having a UV-transparent top and a UV-transparent label. In another embodiment, the container is a blood collection tube, such as a standard red top tube, and the rubber stopper is removed before irradiation.

It is not intended that the invention be limited by the form of the compound. The compound can be added dry and then resuspended when the blood is drawn into the tube. In this manner, the existence of the compound would not be apparent to the phlebotomist.

With respect to new compounds, the present invention contemplates the following base structure:

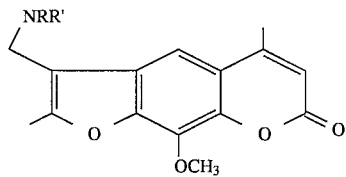

Where R and R'=H, the compound is 4'-aminomethyl-4,5'-dimethyl-8-methoxypsoralen (AMMP). The present invention also contemplates the salt of AMMP.

The present invention further contemplates a stable intermediate, in the synthesis of compounds of the present invention having the following formula:

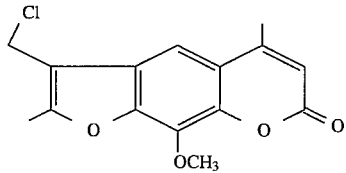

The present invention contemplates binding aminopsoralen compounds to nucleic acid. In one embodiment, the present invention contemplates a complex, comprising this compound bound to nucleic acid. In one embodiment, the binding is covalent. In another embodiment, the binding is non-covalent. In one embodiment, the nucleic acid is selected from the group consisting of viral, bacterial, fungal, mycoplasmal and protozoan nucleic acid.

It is not intended that the present invention be limited by the nature of the nucleic acid bound. The present invention contemplates all forms and sources of RNA and DNA, including Human Immunodeficiency Virus nucleic acid.

It is not intended that the present invention be limited by the method by which the compounds of the present invention are synthesized. In one embodiment, 4'-aminomethyl-4,5'-dimethyl-8-methoxypsoralen (AMMP) is synthesized by the following method: a) providing 4'-chloromethyl-8-methoxy-4,5'-dimethylpsoralen; b) treating 4'-chloromethyl-8-methoxy-4,5-dimethylpsoralen with an alkali salt of phthalimide to give 8-methoxy-4,5'-dimethyl-4'-(phthalimidomethyl)psoralen; and c) treating 8-methoxy-4,5'-dimethyl-4'-(phthalimidomethyl)psoralen with hydrazine or methylamine to yield 4'-aminomethyl-4,5'-dimethyl-8-methoxypsoralen.

In one embodiment 4'-chloromethyl-8-methoxy-4,5'-dimethylpsoralen may be synthesized by the following method: a) providing 4,5'-dimethyl-8methoxypsoralen, b) treating 4,5'-dimethyl-8-methoxypsoralen with chloromethyl methyl ether to yield 4'-chloromethyl-8-methoxy-4,5'-dimethylpsoralen.

DESCRIPTION OF THE FIGURES

FIG. 1 is a side view of one embodiment of a photoactivation device suitable for the practice of the present invention.

FIG. 2 is a side view of the device shown in FIG. 1, in the raised position.

FIG. 3 is a side view of the device shown in FIG. 1, in the lowered position.

FIG. 24 details one compound synthesis scheme of the present invention where the starting material is 4,5'-dimethyl-8-methoxypsoralen.

FIG. 25 details one compound synthesis scheme of the present invention where the starting material is 4'-chloromethyl-4,5'-dimethyl-8-methoxypsoralen.

DESCRIPTION OF THE INVENTION

Figure 4:
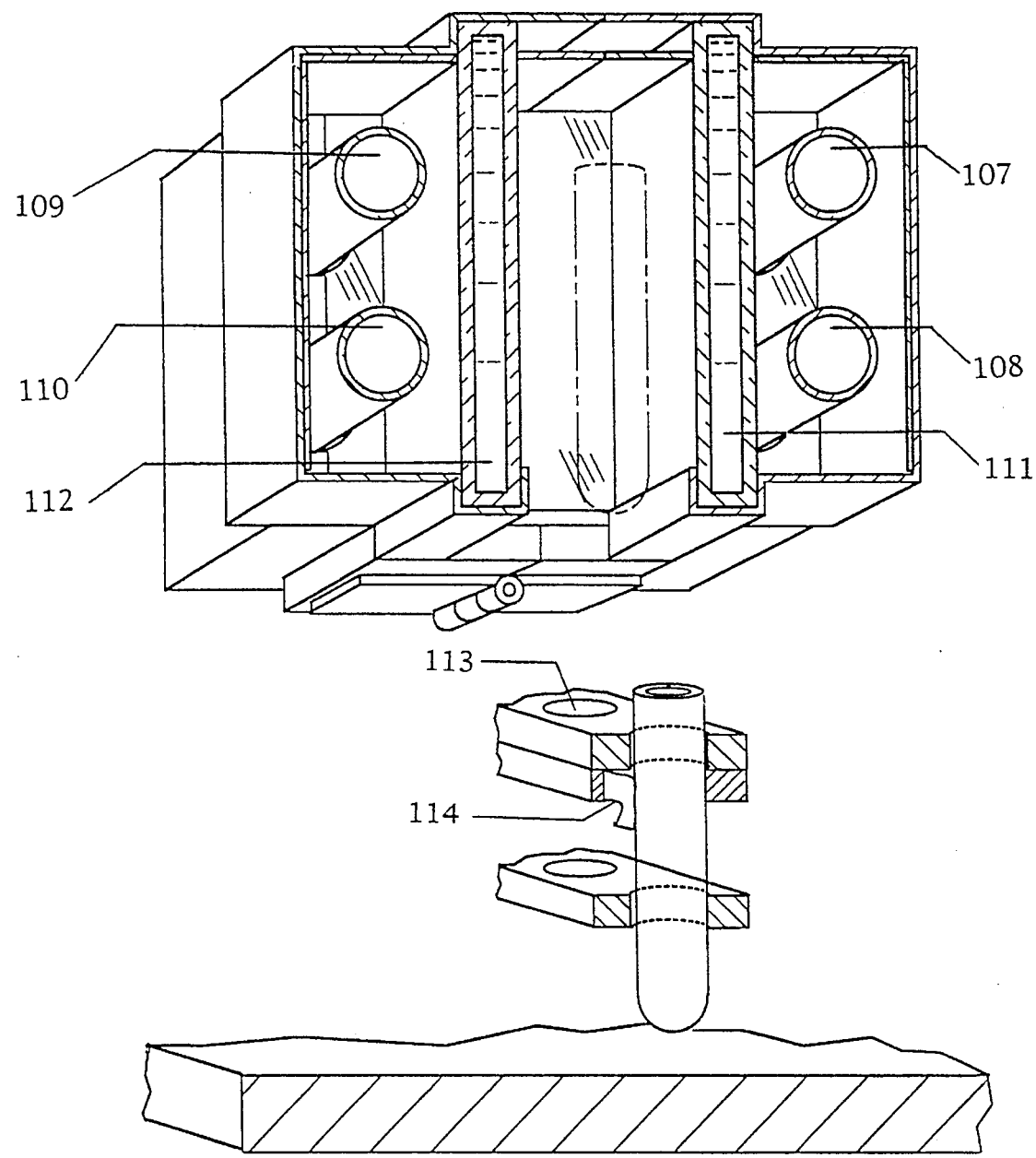
FIG. 4 is a cross sectional view of the device shown in FIG. 2.

The invention generally relates to the inactivation of contaminants in material intended for in vitro use, and in particular the inactivation of pathogens in human fluids prior to clinical testing. As noted previously, in the hospital clinical chemistry laboratory, whole blood is received and these samples are processed to separate the cells from the serum or plasma. These steps involves handling of potentially infectious agents. A process that inactivated pathogens prior to handling and testing would be expected to prevent the transmission of disease.

In one embodiment, the present invention contemplates inactivating human serum after collection but before testing. In this embodiment, a nucleic acid binding compound is selectively employed, such as a furocoumarin. In a preferred embodiment, the furocoumarin is a psoralen that is activated by a photoactivation device.

Psoralens are tricyclic compounds formed by the linear fusion of a furan ring with a coumarin. Psoralens can intercalate between the base pairs of double-stranded nucleic acids, forming covalent adducts to pyrimidine bases upon absorption of long wave ultraviolet light (UVA). G. D. Cimino et al., Ann. Rev. Biochem. 54:1151 (1985). Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977). S. T. Isaacs et al., Trends in Photobiology (Plenum) pp. 279–294 (1982). J. Tessman et al., Biochem. 24:1669 (1985). Hearst et al., U.S. Pat. Nos. 4,124,589, 4,169,204, and 4,196,281, hereby incorporated by reference. Aminopsoralens are defined as psoralens that have amino-substitutions on the 3-, 4-, 5-, 8-, 4'-, or 5'-carbons. The psoralens may or may not have further substitutions, including substitutions on the nitrogen.

Psoralens have been shown to inactivate viruses in some blood products. See H. J. Alter et al., The Lancet (ii:1446) (1988). L. Lin et al., Blood 74:517 (1989). G.P. Wiesehahn et al., U.S. Pat. Nos. 4,727,027 and 4,748,120, hereby incorporated by reference, describe the use of a combination of 8-methoxypsoralen (8-MOP) and irradiation. P. Morel et al., Blood Cells 18:27 (1992) show that 300 μg/mL of 8-MOP together with ten hours of irradiation with ultraviolet light can effectively inactivate viruses in human serum. However, their approach is only feasible if the damage to serum analytes is specifically suppressed by limiting the concentration of molecular oxygen, a difficult and expensive process. Serum analytes are defined here as components sometimes found in blood which are measured in clinical chemistry tests.

The present invention contemplates new photoreactive nucleic acid binding compounds and methods of synthesis of new photoreactive nucleic acid binding compounds. Activation of the new compounds does not result in significant damage to serum analytes.

The inactivation method of the present invention provides a method of inactivating pathogens in human serum, and in particular, viruses prior to clinical testing. In contrast to previous approaches, the method requires only short irradiation times and there is no need to limit the concentration of molecular oxygen. The method serves as protection against a wide range of pathogens without unduly interfering with laboratory operations.

The present invention also contemplates devices for inactivation which activate nucleic acid binding compounds. In one embodiment, the device is an inexpensive source of ultraviolet radiation. In another embodiment, the device provides rapid photoactivation. In yet another embodiment, the device allows for large sample processing. The present invention contemplates devices which can control the temperature of the irradiated samples. These devices are also configured to ensure the inherent safety of the user.

DETAILED DESCRIPTION OF THE INVENTION

The detailed description of the invention is divided into descriptions of I) Photoactivation Devices, IIa) Photoreactive Compounds, IIb) Compound Synthesis, III) Inactivation of Pathogens, IV) Compatibility with Laboratory Protocols, and V) Compatibility with Clinical Testing.

I. PHOTOACTIVATION DEVICES

The present invention contemplates devices and methods for photoactivation and specifically, for activation of photoreactive nucleic acid binding compounds. The present invention contemplates devices having an inexpensive source of electromagnetic radiation that is integrated into a unit. In general, the present invention contemplates a photoactivation device for treating photoreactive compounds, comprising: a) means for providing appropriate wavelengths of electromagnetic radiation to cause activation of at least one photoreactive compound; b) means for supporting a plurality of samples in a fixed relationship with the radiation providing means during activation; and c) means for maintaining the temperature of the samples within a desired temperature range during activation. The present invention also contemplates methods, comprising: a) supporting a plurality of sample containers, containing one or more photoreactive compounds, in a fixed relationship with a fluorescent source of electromagnetic radiation; b) irradiating the plurality of sample containers simultaneously with electromagnetic radiation to cause activation of at least one photoreactive compound; and c) maintaining the temperature of the sample within a desired temperature range during activation.

The major features of one embodiment of the device of the present invention involve: A) an inexpensive source of ultraviolet radiation in a fixed relationship with the means for supporting the sample containers, B) rapid photoactivation, C) large sample processing, D) temperature control of the irradiated samples, and E) inherent safety.

A. Electromagnetic Radiation Source

A preferred photoactivation device of the present invention has an inexpensive source of ultraviolet radiation in a fixed relationship with the means for supporting the sample vessels. Ultraviolet radiation is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g. visible light).

Particular types of ultraviolet radiation are herein described in terms of wavelength. Wavelength is described here in terms of nanometers ("nm"; $10^{-9}$) meters). For purposes herein, ultraviolet radiation extends from approximately 180 nm to 400 nm. When a radiation source, by virtue of filters or other means, does not allow radiation below a particular wavelength (e.g. 320 nm), it is said to have a low end "cutoff" at that wavelength (e.g. "a wavelength cutoff at 300 nanometers"). Similarly, when a radiation source allows only radiation below a particular wavelength (e.g. 360 nm), it is said to have a high end "cutoff" at that wavelength (e.g. "a wavelength cutoff at 360 nanometers").

For any photochemical reaction it is desired to eliminate or least minimize any deleterious side reactions. Some of these side reactions can be caused by the excitation of endogenous chromophores that may be present during the photochemical activation procedure. In a system where only nucleic acid and psoralen are present, the endogenous chromophores are the nucleic acid bases themselves. Restricting the activation process to wavelengths greater than 320 nm minimizes direct nucleic acid damage since there is very little absorption by nucleic acids above 313 nm.

In human serum or plasma, for example, the nucleic acid is typically present together with additional biological constituents. If the biological fluid is just protein, the 320 nm cutoff will be adequate for minimizing side reactions (aromatic amino acids do not absorb above 320 nm). If the biological fluid includes other analytes, there may be constituents that are sensitive to particular wavelengths of light. In view of the presence of these endogenous constituents, it is intended that the device of the present invention be designed to allow for irradiation within a small range of specific and desirable wavelengths, and thus avoid damage to analytes that are to be measured by clinical testing. The preferred range of desirable wavelengths is between 320 and 350 nm.

Some selectivity can be achieved by choice of commercial irradiation sources. For example, while typical fluorescent tubes (BL) emit wavelengths ranging from 300 nm to above 400 nm (with a broad peak centered around 360 nm), BLB type fluorescent lamps are designed to remove wavelengths above 400 nm. This, however, only provides an upper end cutoff.

In a preferred embodiment, the device of the present invention comprises an additional filtering means. In one embodiment, the filtering means comprises a glass cut-off filter, such as a piece of Cobalt glass. In another embodiment, the filtering means comprises a liquid filter solution that transmits only a specific region of the electromagnetic spectrum, such as an aqueous solution of $Co(No_3)_2$. This salt solution yields a transmission window of 320–400 nm. In a preferred embodiment, the aqueous solution of $Co(No_3)_2$ is used in combination with $NiSO_4$ to remove the 365 nm component of the emission spectrum of the fluorescent or arc source employed. The Co—Ni solution preserves its initial transmission remarkably well even after tens of hours of exposure to the direct light of high energy sources.

It is not intended that the present invention be limited by the particular filter employed. Several inorganic salts and glasses satisfy the necessary requirements. For example, cupric sulfate is a most useful general filter for removing the infra-red, when only the ultraviolet is to be isolated. Its stability in intense sources is quite good. Other salts are known to one skilled in the art. Aperture or reflector lamps may also be used to achieve specific wavelengths and intensities.

When ultraviolet radiation is herein described in terms of irradiation, it is expressed in terms of intensity flux (milliwatts per square centimeter or "mW $cm^{-2}$"). "Output" is herein defined to encompass both the emission of radiation (yes or no; on or off) as well as the level of irradiation. In a preferred embodiment, intensity is monitored at 4 locations: 2 for each side of the plane of irradiation.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photoactivation, in one embodiment the present invention employs fluorescent sources to achieve results thus far achievable on only expensive equipment. A preferred fluorescent source is a device ("HRI-100") sold commercially by HRI Research Inc. (Berkeley, Calif. USA) and ULTRA-LUM, INC. (Carson, Calif. USA). The HRI device is described in U.S. Pat. No. 5,184,020, hereby incorporated by reference.

As used here, fixed relationship is defined as comprising a fixed distance and geometry between the sample and the light source during the sample irradiation. Distance relates to the distance between the source and the sample as it is supported. It is known that light intensity from a point source is inversely related to the square of the distance from the point source. Thus, small changes in the distance from the source can have a drastic impact on intensity. Since changes in intensity can impact photoactivation results, changes in distance are avoided in the devices of the present invention. This provides reproducibility and repeatability.

Geometry relates to the positioning of the light source. For example, it can be imagined that light sources could be placed around the sample holder in many ways (on the sides, on the bottom, in a circle, etc.). The geometry used in a preferred embodiment of the present invention allows for uniform light exposure of appropriate intensity for rapid photoactivation. The geometry of a preferred device of the present invention involves multiple sources of linear lamps as opposed to single point sources. In addition, there are several reflective surfaces and several absorptive surfaces. Because of this complicated geometry, changes in the location or number of the lamps relative to the position of the samples to be irradiated are to be avoided in that such changes will result in intensity changes.

B. Rapid Photoactivation

The light source of the preferred embodiment of the present invention allows for rapid photoactivation. The intensity characteristics of the irradiation device have been selected to be convenient with the anticipation that many sets of multiple samples may need to be processed. With this anticipation, a fifteen minute exposure time or less is a practical goal.

In designing the devices of the present invention, relative position of the elements of the preferred device have been optimized to allow for fifteen minutes of irradiation time, so that, when measured for the wavelengths between 320 and 350 nanometers, an intensity flux greater than approximately 1 mW cm$^{-2}$ is provided to the sample vessels.

C. Processing of Large Numbers of Samples

As noted, another important feature of the photoactivation devices of the present invention is that they provide for the processing of large numbers of samples. In this regard, one element of the devices of the present invention is a means for supporting a plurality Of sample containers, and in particular, commercially available red top vacuum tubes. In the preferred embodiment of the present invention the supporting means comprises a tube rack placed between two banks of lights. By accepting commonly used commercially available tubes, the device of the present invention allows for convenient processing of large numbers of samples.

D. Temperature Control

As noted, one of the important features of the photoactivation devices of the present invention is temperature control. Temperature control is important because the temperature of the sample in the sample at the time of exposure to light can dramatically impact the results. For example, conditions that promote secondary structure in nucleic acids also enhance the affinity constants of many psoralen derivatives for nucleic acids. Hyde and Hearst, Biochemistry, 17, 1251 (1978). These conditions are a mix of both solvent composition and temperature. With single stranded 5S ribosomal RNA, irradiation at low temperatures enhances the covalent addition of HMT to 5S rRNA by two fold at 4° C. compared to 20° C. Thompson et al., J. Mol. Biol. 147:417 (1981). Even further temperature induced enhancements of psoralen binding have been reported with synthetic polynucleotides. Thompson et al., Biochemistry 21:1363 (1982).

E. Inherent Safety

Ultraviolet radiation can cause severe burns. Depending on the nature of the exposure, it may also be carcinogenic. The light source of a preferred embodiment of the present invention is shielded from the user. This is in contrast to the commercial hand-held ultraviolet sources as well as the large, high intensity sources. In a preferred embodiment, the irradiation source is contained within a housing made of material that obstructs the transmission of radiant energy (i.e. an opaque housing). No irradiation is allowed to pass to the user. This allows for inherent safety for the user.

IIa. PHOTOREACTIVE COMPOUNDS

"Activation compounds" defines a family of compounds that undergo chemical change in response to triggering stimuli. Triggering stimuli include, but are not limited to, thermal stimuli, chemical stimuli and electromagnetic stimuli.

"Photoreactive, activation compounds" (or simply "photoreactive compounds"), defines a genus of compounds in the activation compound family that undergo chemical change in response to electromagnetic radiation (Table 1).

Table 1. Photoreactive Compounds

Actinomycins
Anthracyclinones
Anthramycin
Benzodipyrones
Fluorenes and fluorenones
Furocoumarins
Mitomycin
Monostral Fast Blue
Norphillin A
Organic dyes
Phenanthridines
Phenazathionium Salts
Phenazines
Phenothiazines
Phenylazides
Polycyclic hydrocarbons
Quinolines
Thiaxanthenones
Thionines One species of photoreactive compounds described herein is commonly referred to as the furocoumarins. The furocoumarins belong to two main categories: 1) psoralens [7H-furo(3,2-g)-(1)-benzopyran-7-one, or δ-lactone of 6-hydroxy-5-benzofuranacrylic acid], which are linear:

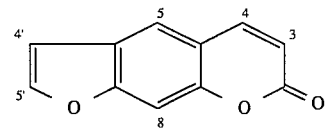

and in which the two oxygen residues appended to the central aromatic moiety have a 1, 3 orientation, and further in which the furan ring moiety is linked to the 6 position of the two ring coumarin system, and 2) the isopsoralens [2H-furo(2,3-h)-(1)-benzopyran-2-one, or δ-lactone of 4-hydroxy-5-benzofuranacrylic acid], which are angular:

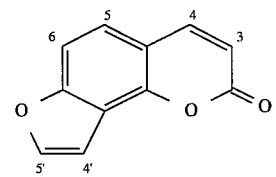

in which the two oxygen residues appended to the central aromatic moiety have a 1, 3 orientation, and further in which the furan ring moiety is linked to the 8 position of the two ring coumarin system. Psoralen derivatives are derived from substitution of the linear furocoumarin at the 3-, 4-, 5-, 8-, 4'-, or 5'-positions, while isopsoralen derivatives are derived from substitution of the angular furocoumarin at the 3-, 4-, 5-, 6-, 4'-, or 5-positions.

The present invention also contemplates new and known photoreactive compounds that inactivate pathogens in red blood cells. One such species of compounds is commonly referred to as the group of red absorbing compounds (absorption of light in the range of 580 nm and above). Like psoralens, red absorbing compounds are small enough to intercalate in a double helix. Thionine (3,7-diaminophenothiazin-5-ium chloride) is an example of a three membered ring with absorption out in the red (commercially available from Sigma Chemical Co., St Louis, Mo.). In this compound, not only are there an N and S in the internal ring, there are two aromatic amines attached to the outer two rings. This compound has been used as a nuclear stain in the past.

IIb. COMPOUND SYNTHESIS

Up to now, 4'-Aminomethyl-4,5',8-trimethylpsoralen (AMT) has been one of most reactive psoralen derivatives, providing up to 1 AMT adduct per 3.5 DNA base pairs. However, AMT is also very efficient in generating active oxygen species, such as singlet oxygen ($^1O_2$) and superoxide radical, which may have adverse effects on clinical chemistry tests of blood products. Table 2 shows the extent of $^1O_2$ production by various psoralens and Methylene Blue relative to 8-MOP. Inspection of Table 2 shows that addition of methoxy groups to the 5- and 8- position of the psoralen scaffold significantly reduces the ability of the psoralen to generate $^1O_2$ (e.g. 5,8-dimethoxypsoralen produces 18-fold less $^1O_2$ than unsubstituted psoralen).

TABLE 2

| Generation of Active Oxygen Species by Psoralen | |
| --- | --- |
| Psoralen Compound | $^1O_2$ production (ave. from 4 expmts) |
| Trimethylpsoralen | 5.3 |
| Psoralen | 3.3 |
| 8-Methoxypsoralen | 1.00 |
| 5-Methoxypsoralen | 0.52 |
| Methylene Blue | 0.49 |
| 5,8-Dimethoxypsoralen | 0.069 |

Based on prior experience with various psoralens, such as AMT, which have greater nucleic acid binding affinities than 8-MOP, but also increased production of active oxygen species, a new psoralen was desired which would have the best characteristics of both 8-MOP and AMT: low active oxygen species generation and high nucleic acid binding affinity. Aminopsoralens were expected to meet such needs. Aminopsoralens are defined as psoralens that have amino-substitutions on the 3-, 4-, 5-, 8-, 4', or 5'-carbons. The psoralens may or may not have further substitutions, including substitutions on the nitrogen.

The first step in synthesizing desirable compounds was to synthesize an intermediate compound from which several compounds of interest could be derived. 4'-Chloromethyl-4,5'-dimethyl-8-methoxypsoralen, Compound 2 of FIG. 24, was designed to be such an intermediate.

As shown in FIG. 24, the synthesis pathway for the compounds of the present invention involves starting with the following compound, Compound 1:

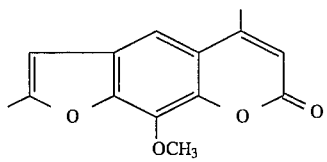

This starting compound in the synthesis of Compound 2 is 4,5'-dimethyl-8-methoxypsoralen. The synthesis of this precursor compound has been described previously in the literature. See Bender, et al., J. Org. Chem. 44:2176 (1979). Alternatively, the starting compound may be synthesized by the following method: 8-acetyl-7-(2-chloroallyl)oxy-4-methylcoumarin, described in Bender, et al., J. Org. Chem. 48:2709 (1983), is initially oxidized to a phenolic compound, 7-(2-chloro-2-propenyl)oxy-8-hydroxy-4-methylcoumarin, and then methylated, providing 7-(2-chloro-2-propenyl)oxy-8-methoxy-4-methylcoumarin. Claisen rearrangement provides 6-(2-chloro-2-propenyl)-7-hydroxy-8-methoxy-4-methylcoumarin, which is then converted to 4,5'-dimethyl-8-methoxypsoralen.

FIG. 25 shows chloromethylation of this compound (1), giving 4'-chloromethyl-8-methoxy-4,5'-dimethylpsoralen (2). From this intermediate, several compounds of the present invention can be synthesized. For example, 4'-aminomethyl-4,5'-dimethyl-8-methoxypsoralen (AMMP), which exhibits the desired low active oxygen species generation and high nucleic acid binding affinity, may be synthesized as shown in FIG. 25. 4'-Chloromethyl-8-methoxy-4,5'-dimethylpsoralen (2), is converted via Gabriel synthesis to AMMP (4) in two steps.

In addition, various N-substituted and N,N'-disubstituted analogs (e.g. in which R and/or R' is alkyl or substituted alkyl) which have similar activity may be synthesized by the following method. 4'-Chloromethyl-8-methoxy-4,5'-dimethylpsoralen can be converted to a secondary or tertiary amine by reaction with the appropriate primary or secondary amine precursor, HNRR' where R and/or R' are linear or branched alkyls (C1–C20) or alkyls substituted with, for example, hydroxyl, alkoxy, amino, thio or mercapto groups. 4'-Chloromethyl-8-methoxy-4,5'-dimethylpsoralen is stirred with an excess of amine either neat or in the presence of solvent such as ethanol, at 25°–100° C., to produce a secondary or tertiary amine derivative.

The present invention also contemplates methods of synthesizing biotinylated aminopsoralens. While not required, it may be useful to be able to remove the photoreactive nucleic acid binding compounds of the present invention from the decontaminated material once inactivation is complete. The present invention contemplates using biotinilated compounds as photoreactive nucleic acid binding compounds. These compounds may then be removed from material using such approaches as binding to avidin, a protein specific to biotin, which is attached to a solid support or magnet beads. Thus, after the material has been decontaminated, it is contacted with the supported avodin, which then removes the photoreactive compound from the treated material. In one embodiment, a biotinilated derivative useful in such a filtration system is synthesized as follows: 4'-Chloromethyl-8-methoxy-4,5'-dimethylpsoralen is treated with 1,2-bis-(2-methylamino)ethoxyethane, to produce 4'-[N-methyl-N-(8-methylamino-3,6-dioxa)octylamino]methyl-4,5'-dimethyl-8-methoxypsoralen, (i.s. a variation of the base structure, where R=CH$_3$ and R'=CH$_2$CH$_2$OCH$_2$CH$_2$OCH$_2$CH$_2$NHCH$_3$). 4'-[N-Methyl-N-(8-methylamino-3,6-dioxa)octylamino]methyl-4,5'-dimethyl-8-methoxypsoralen is treated with biotin-amidocaproate N-hydroxysuccinimide ester to produce the biotinilated compound, 5-(biotinamido)caproic acid N-[N,N'-Dimethyl-3,6-dioxa-N'-(8-methyloxy-4,5'-dimethylpsoralen-4-yl)methyl]-1,8-octanediamine amide, (referred to as "5B-AMMP" in Example 6 and Example 11, below).

The present invention also contemplates methods of synthesizing radiolabelled photoreactive nucleic acid binding compounds. For example, radiolabelled AMMP can be synthesized as follows: 4'-chloromethyl-4,5'-dimethyl-8-methoxypsoralen is hydrolized to 4'-hydroxymethyl-4,5'-dimethyl-8-methoxypsoralen. Oxidation of 4'-hydroxymethyl-4,5'-dimethyl-8-methoxypsoralen with chromium trioxide gives 4'-formyl-4,5'-dimethyl-8-methoxypsoralen, which is then reduced with tritiated sodium borohydride to produce. 4'-hydroxy[$^3$H]methyl-8-methoxy-4,5'-dimethylpsoralen is treated with thionyl chloride to yield the tritiated analog of 4'-chloromethyl-4,5'-dimethyl-8-methoxypsoralen. This is then converted to [$^3$H]AMMP by Gabriel synthesis as previously described for AMMP.

III. INACTIVATION OF PATHOGENS

The present invention contemplates treating blood with photoreactive activation compound and irradiating to inactivate all contaminating pathogen nucleic acid sequences before using the blood in clinical chemistry tests.

A. Inactivation In General

As herein defined, something is "inactivated" when it is rendered incapable of replication. The term "inactivation" is here defined as the altering of the nucleic acid of a pathogen so as to render the pathogen incapable of replication.

Inactivation "sensitivity" is an operationally defined term. It is defined only in the context of an "inactivation method" and the particular detection method that is used to measure organisms remaining. Inactivation sensitivity is the number of germination seeds (e.g., viable bacterial cells) that must be present to result in a measurable signal in some defined detection assay following an inactivation procedure.

To appreciate that an "inactivation method" may or may not achieve "inactivation," it is useful to consider a specific example. A bacterial culture is said to be inactivated if an aliquot of the culture, when transferred to a fresh culture plate and permitted to grow, is undetectable after a certain time period. The time period and the growth conditions (e.g. temperature) define an "amplification factor". This amplification factor along with the limitations of the detection method (e.g. visual inspection of the culture plate for the appearance of a bacterial colony) define the sensitivity of the inactivation method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the "inactivation method" appears to be completely effective (and above which "inactivation" is, in fact, only partially effective). This interplay between the amplification factor of an assay and the threshold that the detection method defines, can be illustrated. Referring now to Table 3, bacterial cells are applied to a plate under two different sets of conditions: in one case, the growth conditions and time are such that an overall amplification of $10^4$ has occurred; in the other case, the growth conditions and time are such that an overall amplification of $10^8$ has occurred. The detection method is arbitrarily chosen to be visual inspection. The detectable signal will be proportional to the number of bacterial cells actually present after amplification. For calculation purposes, the detection threshold is taken to be $10^6$ cells; if fewer than $10^6$ cells are present after amplification, no cell colonies are visually detectable and the inactivation method will appear effective, i.e. it would be "substantially inactivated." Given the amplification factor of $10^4$ and a detection threshold of $10^6$, the inactivation sensitivity limit would be 100 bacterial cells; if less than 100 viable bacterial cells were present in the original aliquot of the bacterial culture after the inactivation method is performed, the culture would still appear to be inactivated.

TABLE 3

| AMPLI-FICATION FACTOR | # OF VIABLE BACTERIAL CELLS APPLIED TO A PLATE | | | | |
|---|---|---|---|---|---|
| | 1 | 10 | 100 | 1000 | |
| $10^4$ | $10^4$ | $10^5$ | $10^6$ | $10^7$ | # of bacterial cells cells after amplification |
| | − | — | + | ++ | Detection (+/−) |
| $10^8$ | $10^8$ | $10^9$ | $10^{10}$ | $10^{11}$ | # of bacterial cells after amplification |
| | ++ | +++ | +++ | ++++ | Detection (+/−) |

Alternatively, if the time and growth conditions permitted an amplification of $10^8$, then the inactivation sensitivity limit (assuming the same detection threshold) would be 1 bacterial cell. Under the latter conditions, the inactivation method must be sufficiently stringent that all bacterial cells are, in fact, incapable of replication for inactivation to appear complete (i.e. the inactivation method would need to cause inactivation, not just substantial inactivation).

B. Inactivation of Potential Pathogens

The same considerations of detection threshold and amplification factor are present when determining the sensitivity limit of a inactivation method for nucleic acid. Again, by "inactivation" it is meant that the nucleic acid is rendered incapable of replication.

The inactivation method of the present invention renders nucleic acid in pathogens substantially unamplifiable. In one embodiment, the inactivation method renders pathogen nucleic acid in blood preparations unamplifiable. Also, in one embodiment, the inactivation method of the present invention renders pathogen DNA in clinical samples substantially unamplifiable.

It is not intended that the inactivation method of the present invention be limited by the nature of the nucleic acid; it is contemplated that the inactivation method render all forms of nucleic acid (whether DNA, mRNA, etc.) substantially unamplifiable.

While it is not intended that the present invention be limited to any theory by which nucleic acid is rendered substantially unamplifiable by the methods and compounds, it is expected that inactivation occurs by either 1) modification of nucleic acid, or 2) inhibition of the amplification enzyme itself. Again, while not limited to any mechanism, it is expected that, if modification of nucleic acid occurs with inactivation compounds, it probably occurs because the compounds react with nucleic acid to create sufficient adducts per base (i.e. sufficient "modification density") such that statistically all strands are prevented from either 1) subsequent use of the denatured nucleic acid in single stranded form as template for amplification or 2) dissociation of the double stranded form of the nucleic acid into single strands, thereby preventing it from acting as a template for subsequent amplification.

In the case of activation compounds modifying nucleic acid, it is preferred that interaction of the pathogen nucleic acid (whether DNA, mRNA, etc.) with the activation compound makes the pathogen unable to replicate, so that infection will not result should a human be exposed to the pathogen.

IV. COMPATIBILITY WITH LABORATORY PROTOCOLS

As explained above, health care clinicians handle great volumes of blood every day. This intensive handling of potentially infectious human fluids poses a grave health risk. In response to this problem, the present invention contemplates methods and compositions for inactivating contaminants in material intended for in vitro use, and in particular inactivating pathogens in human fluids prior to clinical testing.

The inactivation methods of the present invention are adaptable to the clinical laboratory. The large volume Of human serum handled daily could be processed according to the present invention without significantly changing the laboratory practice.

The general procedure used in clinical laboratories today is as follows: blood is drawn from a patient into a blood collection tube. A blood collection tube is defined as a tube into which blood is drawn. The specific type of tube generally used is a "clot" tube ("red top" tube). The tube is then centrifuged to separate serum from red blood cells, the tube is reopened by removing the rubber stopper by hand, plastic inserts are manually pushed down into the serum to a level just above the packed cells to maintain the serum/red blood cell separation, serum is then pipetted from the top of the insert into a sample cup which is placed in a processing rack for analysis. At the point of tube opening after the centrifugation step, and in each subsequent step requiring manual manipulations, the laboratory clinician is exposed to whatever pathogens the blood may carry. An embodiment of the present invention Contemplates inactivating any pathogens in the blood before the tube is opened.

Since centrifugation is already used, the laboratory is accustomed to some "sample preparation" before the serum goes to the instrument. Without intending to be limited to any embodiment of the present invention, the invention contemplates a preferred embodiment where a nucleic acid binding compound could be added to the tube at the point of tube manufacture. In one embodiment, this compound is an aminopsoralen, such as AMT or AMMP. The compound could be added dry and then could be resuspended when the blood is drawn into the tube.

When the tube arrives at the lab, the clinician centrifuges it in the usual manner. Without intending to be limited to any time sequence for activation of the binding compound, the present invention contemplates an embodiment where after centrifugation, the tube is irradiated in a photoinactivation device of the present invention. This light device is designed to accommodate the standard commercially available red top vacuum tubes commonly used in clinical laboratories (Available from Terumo Medical, Elkton, Md.). Irradiation activates the photoreactive binding compound which then binds nucleic acids, inactivating any pathogen nucleic acid in the blood sample. The tube would then be opened and processed as before, but free from the risk of exposure to hazardous blood born pathogens.

As a result of growing concern over the spread of HIV, some clinical laboratories have abandoned the use of inserts and implemented the use of a "gel" that is in the empty tube at the time the blood is drawn. The tube is centrifuged and the red cells go below the gel while the serum remains above. In one embodiment of the present invention, the tube could be placed in a photoactivation device of the present invention which exposes only the gel and the serum to UV transmission. The rest of the tube would be protected from UV, thereby avoiding any deleterious effects to the red blood cell fraction from UV exposure. Widespread use of the gell filled tubes proves that the addition of substances to a tube at the point of manufacture is a feasible and necessary approach to combating the spread of infectious diseases.

IV. COMPATIBILITY WITH CLINICAL TESTING

A major concern is whether the decontamination process interferes with the chemistry tests. Clearly, one does not want to inactivate pathogens and render the serum or plasma unusable for testing.

Without wishing to be bound to any theory by which damage to clinical chemistry samples occurs, it is contemplated that free oxygen radicals, generated by ultraviolet irradiation of some photoreactive chemicals, change the results of clinical chemistry tests. These oxygen species have adverse effects on some clinical chemistry tests of blood products (see table 2, above). AMT is very efficient in generating active oxygen species, such as singlet oxygen ($^1O_2$) and superoxide radical.

The new psoralen derivative, AMMP, and other aminopsoralens have been designed structurally similar to AMT, to maintain the high reactivity with nucleic acid provided by such a structure. Yet it is modified by the addition of a methoxy group to the 8 position of the central ring, in place of an hydroxy group. Without intending to be limited by any description of the process by which this invention operates, it is presumed that this modification minimizes the generation of active oxygen species. It is expected that hydroxygroups on the 8 position of AMT are converted into singlet oxygen during radiation with UV. It is believed that this modification improves upon both AMT and 8-MOP by providing the favorable characteristics of AMT for inactivation of pathogens in blood products while concurrently preserving cellular and protein functions that are measured by the clinical tests. Most importantly, the inactivation can be carried out in the presence of oxygen.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); µL(microliters); cm (centimeters); mm (millimeters); µm (micrometers); nm (nanometers); Å(Angstrom); Ci (Curie); mCi (milliCurie); °C. (degrees Centigrade); HPLC (High Pressure Liquid Chromatography); TLC (Thin Layer Chromatography); EAA (ethyl-acetoacetate); DMF (N,N-dimethylformamide); DCP (dichloropropene); EtOH (ethanol); HOAc (acetic acid); BP (base pair); kBP (kilobase pair); BUN (blood urea nitrogen); Creat (creatinine); phos acid (phosphoric acid); alk (alkaline phosphatase); ALT (Alanine Aminotransferase); AST (Aspartate Transaminase); LDH (lactose dehydrogenase); CPK (creatinine kinase); W (watts); mW (milliwatts); ~(approximately).

EXAMPLE 1

As noted above, the present invention contemplates devices and methods for the activation of photoreactive nucleic acid binding compounds. In this example, a photoactivation device for decontaminating human serum or plasma samples according to the method of the present invention is described. This device has the following features: 1) an inexpensive source of electromagnetic radiation, 2) temperature control of the sample, 3) a multi-sample holder, 4) a multiple sample irradiation format, and 5) a compact design that requires minimal bench space. This device comprises: a) means for providing appropriate wavelengths of electromagnetic radiation to cause activation of at least one photoreactive compound; b) means for supporting a plurality of samples in a fixed relationship with the radiation providing means during activation; and c) means for maintaining the temperature of the samples within a desired temperature range during activation.

FIG. 1 is a side view of one embodiment of the device integrating the above-named features. The figure shows the bottom platform of an opaque housing (100), joined to an opaque cover (101) which is supported in a raised position by four legs (two legs shown, 102A and 102C). The legs are each jointed at their center, the center joints (103A and 103C) and at the points the legs attach to the bottom platform (not shown) and to the cover (not shown), permitting the cover to be lowered to rest on the bottom platform. This provides user protection from electromagnetic radiation emitted by a plurality of bulbs within the cover (shown as dashed lines in FIG. 1.) A handle (104), located at one end of the cover, where one pair of legs meets the cover, can be pivoted to raise and lower the cover.

The cover fits over a rack (105) resting on the bottom platform, having a plurality of intrusions (not shown) for supporting a plurality of sample vessels (106). It is not intended that the present invention be limited by the nature of the material used to form the rack (105), bottom platform (100), or cover (101). In one embodiment, they are formed with a substance that does not transmit ultraviolet light, thereby protecting the user. In another embodiment, the rack (105) is formed in part by a substance that does not transmit ultraviolet light, and in part by a substance transparent to ultraviolet light. This allows for selective irradiation of only sections of the sample vessels (106).

FIG. 2 is a side view Of the invention shown in FIG. 1, in the raised position. FIG. 2 shows the legs (102A and 102B) folding at the center joints (103A and 103B) as the cover (101) is lowered slightly from the raised position. The handle (104) has been rotated approximately 45 degrees from vertical to achieve the lowering of the cover. FIG. 2 also shows how the cover is positioned over the rack (105) and sample vessels (106).

FIG. 3 is a side view of the invention shown in FIG. 1, in the lowered position. FIG. 3 shows the cover (101) in the fully lowered position resting on the bottom platform (100). The handle (104) is rotated almost 90 degrees from vertical to achieve the fully lowered position.

FIG. 4 is a cross sectional view of the invention shown in FIG. 2. FIG. 4 shows the cover (101) having four bulbs (107–110) connectable to a power source (not shown). The bulbs serve as a source of electromagnetic radiation and, in one embodiment, ultraviolet radiation. While not limited to the particular bulb type, the embodiment is configured to accept an industry standard, F8T5BL hot cathode dual bipin lamp.

When the cover is in the lowered position, the rack (105) and sample vessels (106) are exposed to irradiation from the bulbs (107–110) on two sides. The bulbs (107–110) are separated from the sample vessels by two chambers (111 and 112). It is not intended that the present invention be limited by the nature of the material used to form the chambers (111 and 112). In one embodiment, they are made of glass. In another embodiment, they are made of a glass cut-off filter, such as a piece of Cobalt glass. In another embodiment, they are made of plastic. In a preferred embodiment, they are made of UV transmitting acrylic selected from the group of commercial acrylics consisting of ACRYLIC-UVT (Polycast), PLEXIGLAS 11-UVT (Rohm & Haas), PLEXIGLAS G-UVT (Rohm & Haas) and ACRYLITE OP-4 (Cyro). In one embodiment, the chambers contain a liquid filter solution that transmits only a specific region of the electromagnetic spectrum. In a preferred embodiment, the chambers contain an aqueous solution of $Co(No_3)_2$. This salt solution yields a transmission window of 320–400 nm. In a preferred embodiment, the aqueous solution of $Co(NO_3)_2$ is used in combination with $NiSO_4$ to remove the 365 nm component of the emission spectrum of the fluorescent or arc source employed.

FIG. 4 shows the rack (105) is punctuated with sample holder intrusions (113). Each sample holder intrusion (113) has an adjustable tube holder (114) which allows a sample tube to be placed securely in the rack in a variety of positions.

Figure 5:
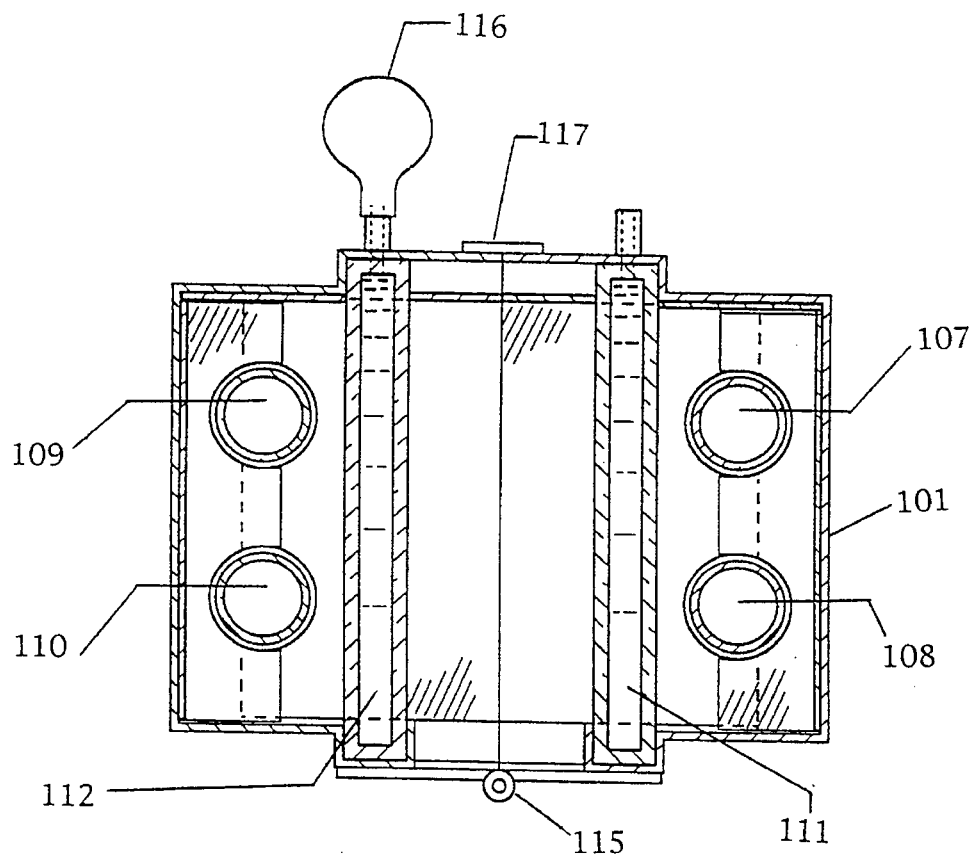
FIG. 5 is a cross-sectional view of the device shown in FIG. 2 in the closed position.

FIG. 5 is a cross sectional view of the cover (101) of the device shown in FIG. 2. FIG. 5 shows the cover (101) having four bulbs (107–110) connectable to a power source (not shown). FIG. 5 also shows one of the opening joints (115) where the two halves of the cover (101) are linked. The opening joints allow the cover (101) to be opened for cleaning. The opening handle (116) is provided to open the cover (101). When the cover is closed, the latch (117) holds the cover secure.

Figure 6:
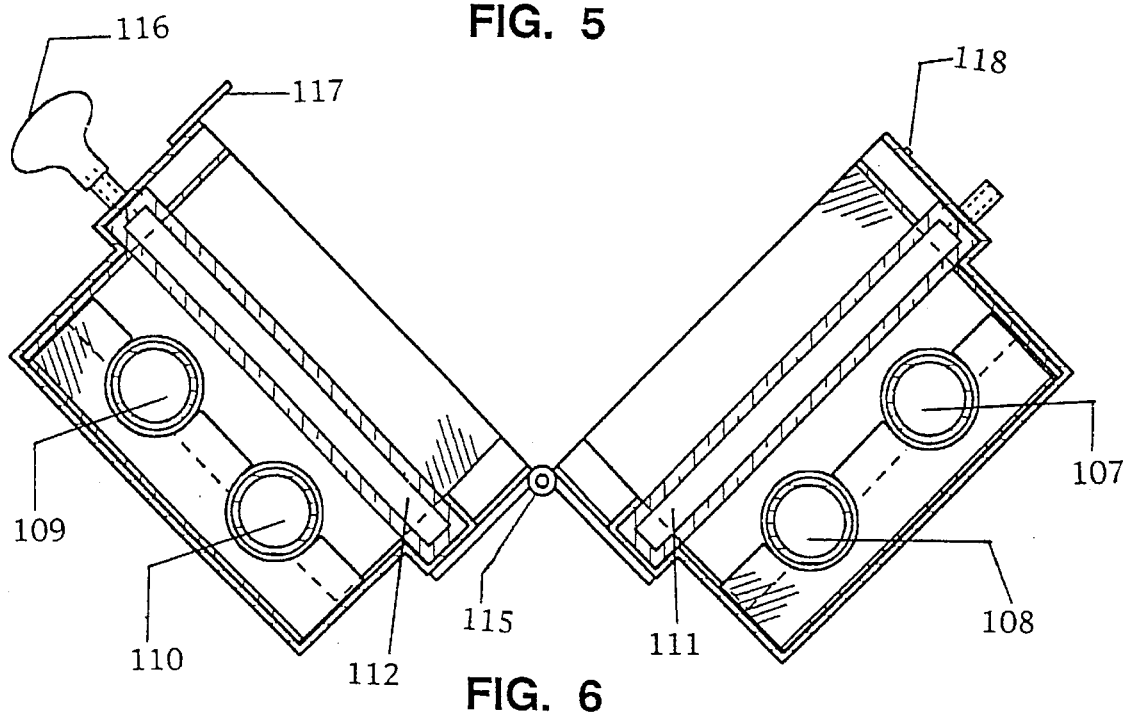
FIG. 6 is a cross-sectional view of the device shown in FIG. 2, in the open position.

FIG. 6 is a cross sectional view of the cover (101) of the device shown in FIG. 2, in the open position. FIG. 6 is a view of the device shown in FIG. 5, in the open position, rotated at the opening joint (115). FIG. 6 shows the clasp (118) onto which the latch (117) is secured when the cover (101) is in the closed position.

Figure 7:
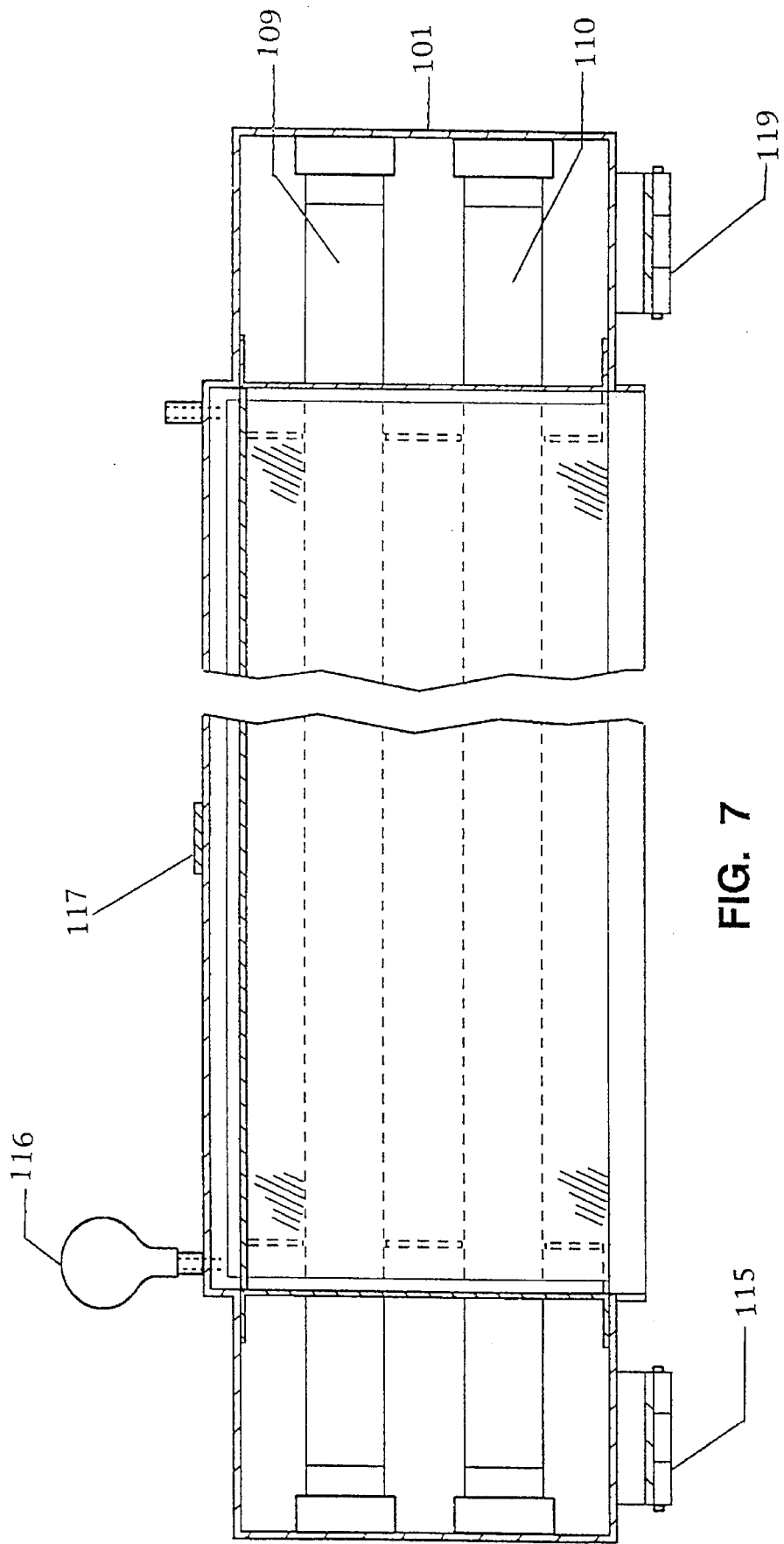
FIG. 7 is a cross sectional view of the device shown in FIG. 1.

FIG. 7 is a cross sectional view of the cover (101) of the device shown in FIG. 1. FIG. 7 shows both opening joints (115, 119) connected to the bottom of the cover (101). FIG. 7 also shows two of the bulbs (109, 110) connectable to a power source (not shown).

Figure 8:
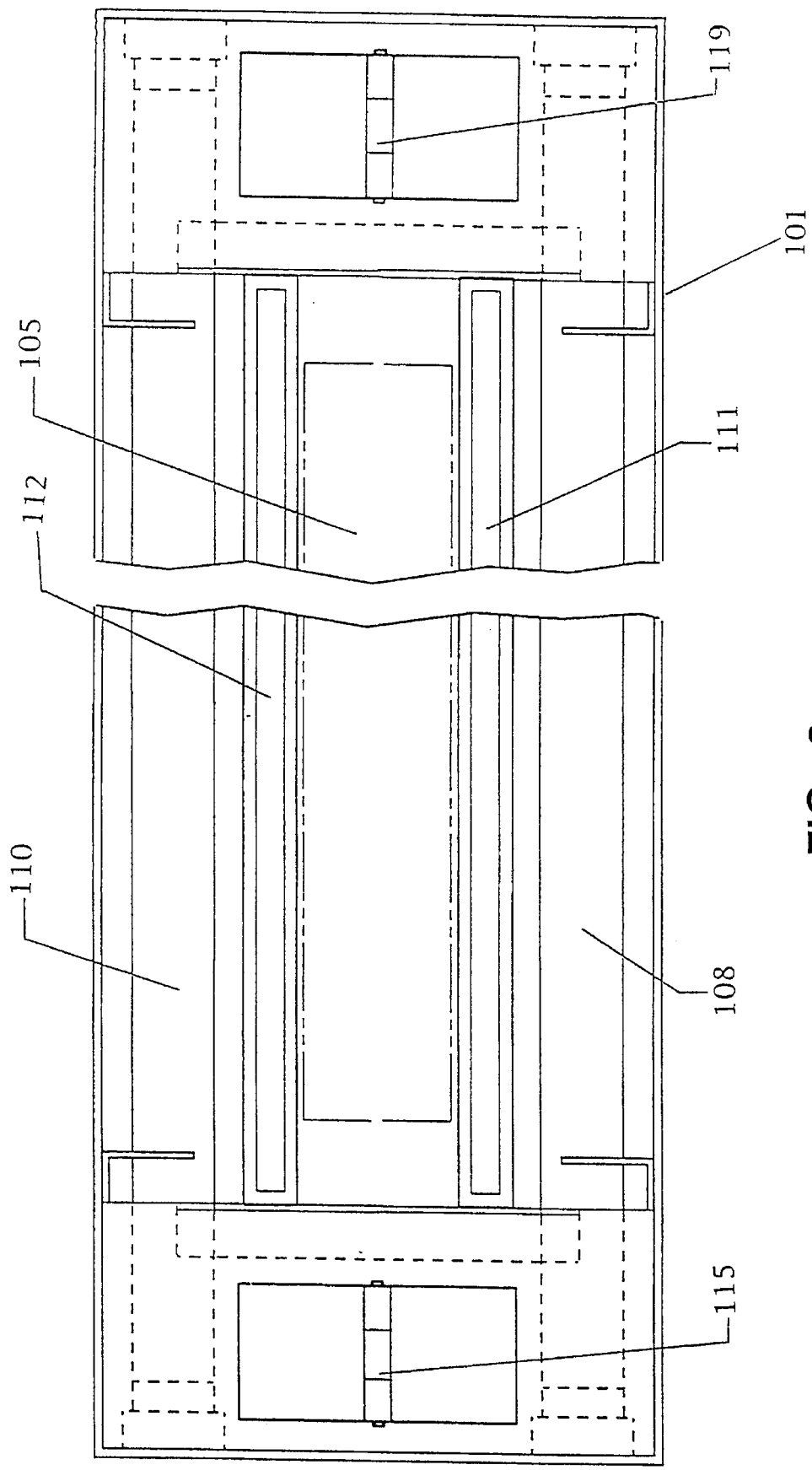
FIG. 8 is a cross sectional view of the bottom of the cover of the device shown in FIG. 1.

FIG. 8 is a cross sectional view of the bottom of the cover (101) of the device shown in FIG. 1. It shows the opening joints (115, 119) attached to the cover (101). FIG. 8 also shows two of the bulbs (108, 110) connectable to a power, source (not shown) which are separated from the sample vessels (not shown) in the rack (105) by two chambers (111 and 112).

Figure 9:
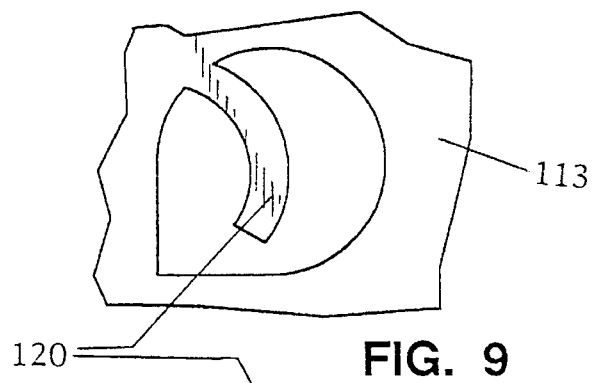
FIG. 9 is a perspective view of a tube holder device of the present invention.

FIG. 9 is a perspective view of a tube holder device of the present invention, found in the sample holder intrusion (113), as shown in FIG. 4. The tube holder (120) is made of a flexible material that allows a tube (not shown) to be inserted into the sample holder intrusion (113) and provides resistance from tube movement.

Figure 11:
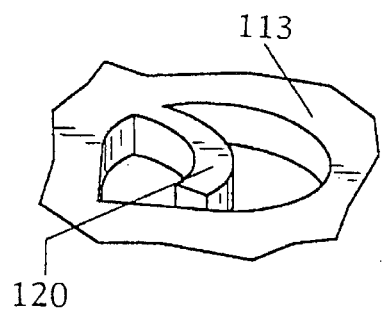
FIG. 11 is a perspective view of a tube holder device of the present invention.
Figure 10:
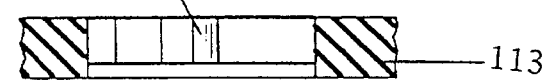
FIG. 10 is a cross sectional view of the device shown in FIG. 9.

FIG. 10 is a cross sectional view of the tube holder device shown in FIG. 9. FIG. 11 is a side view of the tube holder device shown in FIG. 9.

Figure 12:
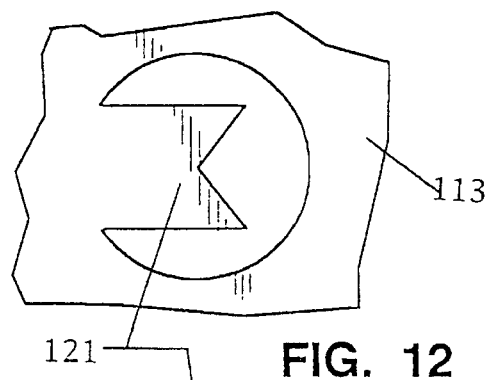
FIG. 12 is a perspective view of a tube holder device of the present invention.

FIG. 12 is a perspective view of another tube holder device of the present invention, found in the sample holder intrusion (113), as shown in FIG. 4. The tube holder (121) is made of a flexible material that allows a tube (not shown) to be inserted into the sample holder intrusion (113) and provides resistance from tube movement.

Figure 14:
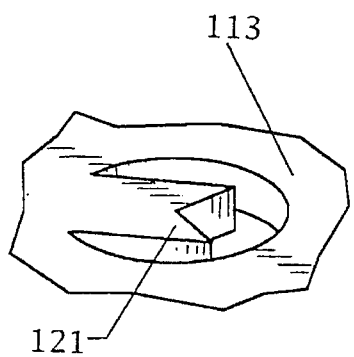
FIG. 14 is a perspective view of a tube holder device of the present invention.
Figure 13:
FIG. 13 is a cross sectional view of the device shown in FIG. 12.

FIG. 13 is a cross sectional view of the device shown in FIG. 12, exhibiting the flexibility feature of the tube holder (121). FIG. 14 is a perspective view of the tube holder device shown in FIG. 12.

Figure 15:
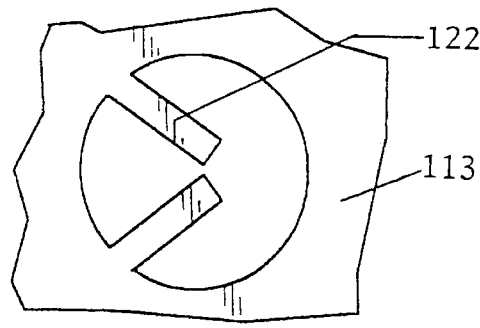
FIG. 15 is a perspective view of a tube holder device of the present invention.

FIG. 15 is a perspective view of another tube holder device of the present invention, found in the sample holder intrusion (113), as shown in FIG. 4. The tube holder (122) is made of a flexible material that allows a tube (not shown) to be inserted into the sample holder intrusion (113) and provides resistance from tube movement.

Figure 17:
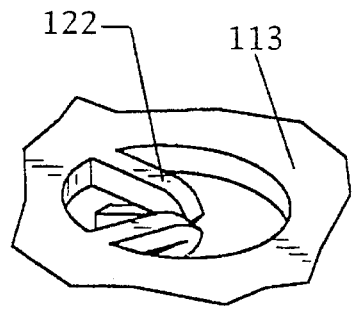
FIG. 17 is a perspective view of the device shown in FIG. 15.
Figure 16:
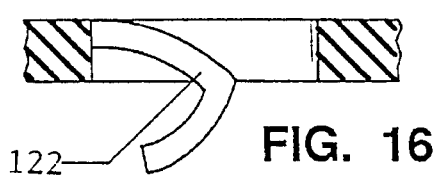
FIG. 16 is a cross sectional view of the device shown in FIG. 15.

FIG. 16 is a cross sectional view of the device shown in FIG. 15, exhibiting the flexibility feature of the tube holder (122). FIG. 17 is a perspective view of the device shown in FIG. 15.

EXAMPLE 2

Figure 18:
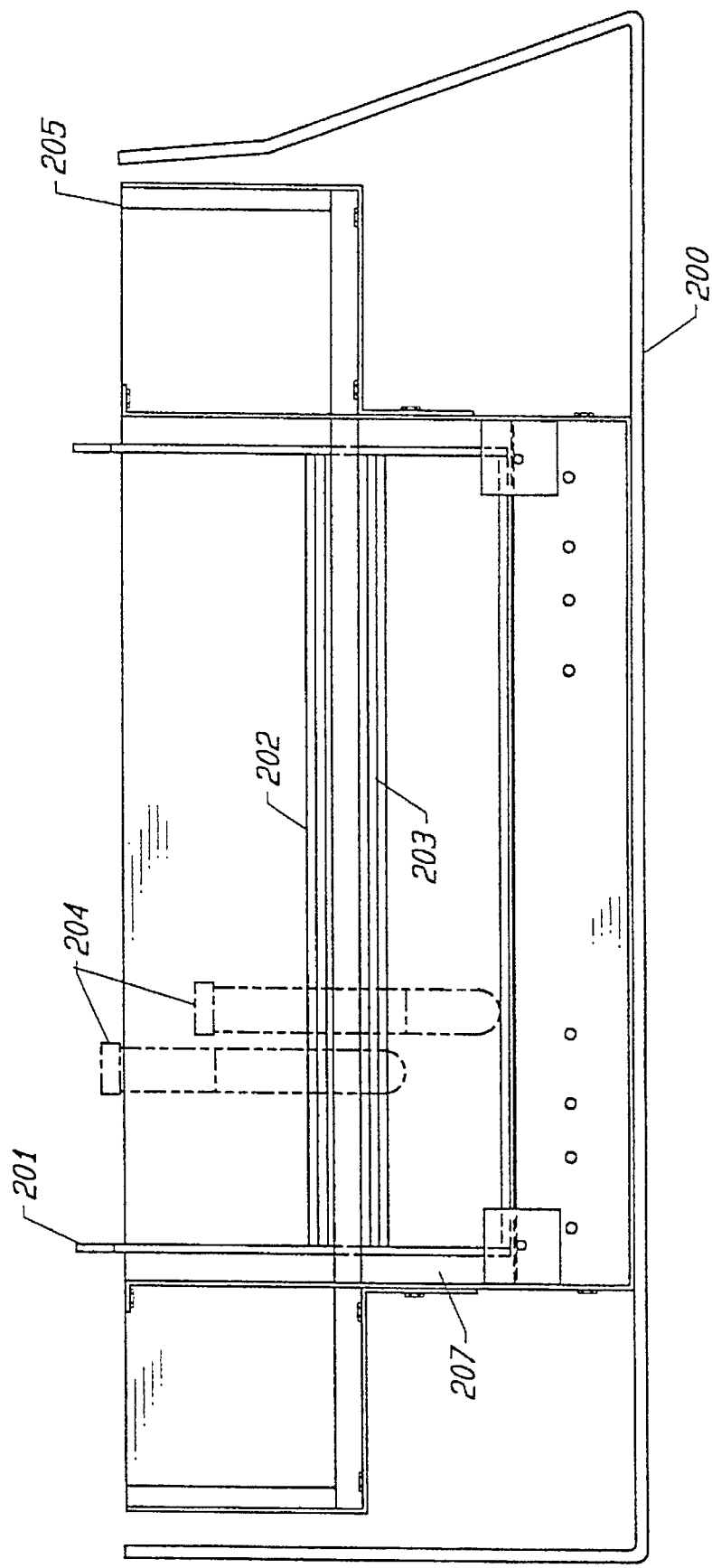
FIG. 18 is a cross sectional view of one embodiment of a photoactivation device suitable for the practice of the present invention.

In this example, a second embodiment of a photoactivation device for decontaminating human serum or plasma samples according to the method of the present invention is described. This embodiment is hereinafter referred to as "the Device of Example 2". FIG. 18 is a cross section of this embodiment. The figure shows the bottom platform of an opaque housing (200), in which rests a removable rack (201). The rack (201) has two tube supports (202, 203) each having a plurality of sample holder intrusions (not shown) for supporting a plurality of sample vessels (204). It is not intended that the present invention be limited by the nature of the material used to form the rack (201) or housing (200). In one embodiment, they are formed with a substance that does not transmit ultraviolet light, thereby protecting the user. In another embodiment, the rack is formed in part by a substance that does not transmit ultraviolet light, and in part by a substance transparent to ultraviolet light. This allows for selective irradiation of only sections of the sample vessels (204). In one embodiment, the tube supports (202, 203) are constructed 0f one sheet of flexible material, such as rubber, positioned between two sheets of rigid material, such as plastic, to provide adjustable sample holder intrusions to support sample vessels (204) in various positions in the tube supports (202, 203).

The opaque housing (200), as well as a removable UV opaque cover (not shown) that fits over the cavity in which the rack (201) rests, provides user protection from electromagnetic radiation emitted by a plurality of bulbs within the cover (not shown).

The two light source housings (205, only one shown) are situated one in front of the rack (201) and one behind the rack. The light sources (not shown) are fixed within the light source housings (205) and are separated from the rack (201) by two chambers (207, only one shown). Each chamber is situated between one light source housing (205) and the rack (201). It is not intended that the present invention be limited by the nature of the material used to form the chambers (207). In one embodiment, they are made of glass. In another embodiment, they are made of a glass cut-off filter, such as a piece of Cobalt glass. In another embodiment, they are made of plastic. In a preferred embodiment, they are made of UV transmitting acrylic selected from the group of commercial acrylics consisting of ACRYLIC-UVT (Polycast), PLEXIGLAS 11-UVT (Rohm & Haas), PLEXIGLAS G-UVT (Rohm & Haas) and ACRYLITE OP-4 (Cyro). In one embodiment, the chambers contain a liquid filter solution that transmits only a specific region of the electromagnetic spectrum. In a preferred embodiment, the chambers contain an aqueous solution of $Co(No_3)_2$. This salt solution yields a transmission window of 320–400 nm. In a preferred embodiment, the aqueous solution of $Co(NO_3)_2$ is used in combination with $NiSO_4$ to remove the 365 nm component of the emission spectrum of the fluorescent or arc source employed.

Figure 19:
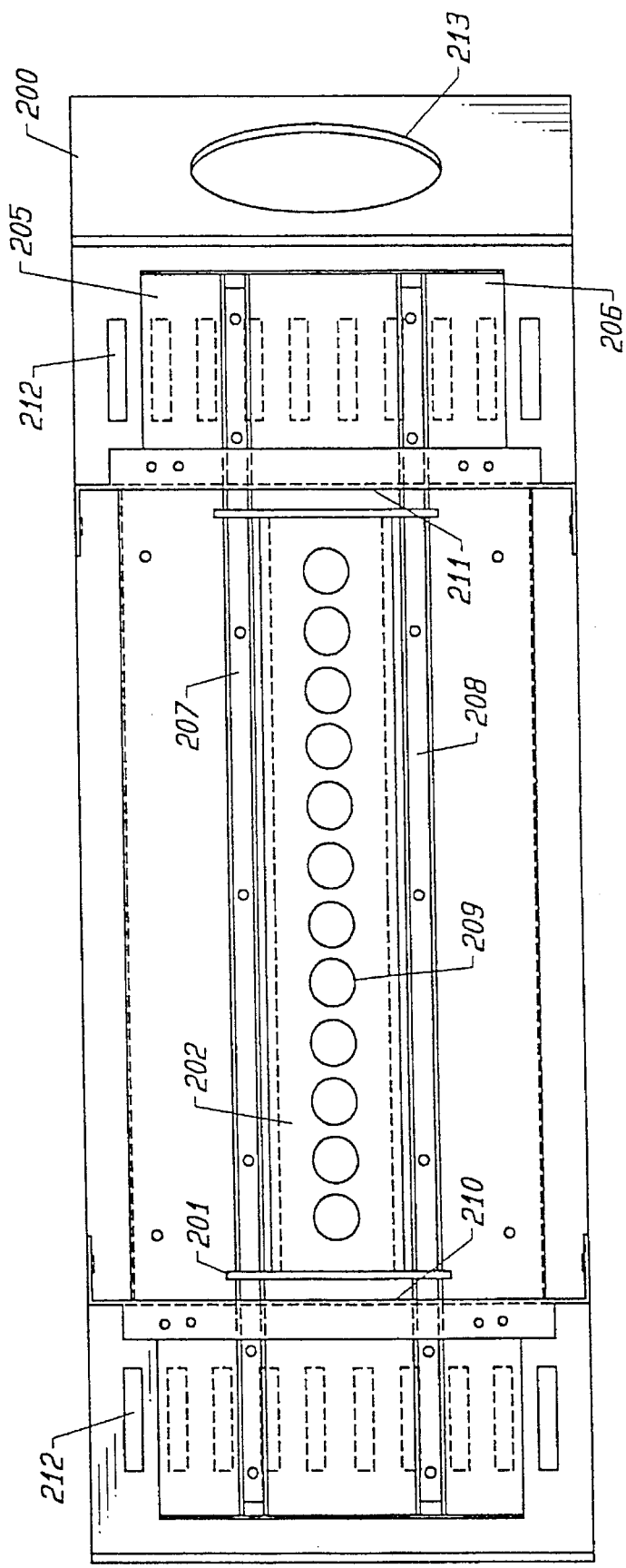
FIG. 19 is a cross sectional view of the top of the device shown in FIG. 18.

FIG. 19 is a cross sectional view of the device of FIG. 18 from the top of the device of FIG. 18. FIG. 18 shows the rack (201) within the opaque housing (200). The rack (201) has a plurality of sample holder intrusions (209) which hold the sample vessels. The rack (201) is bounded on two sides by the chambers (207, 208) which filter the light from the UV light sources (not shown) within the light source housings (205, 206). The rack (201) is also bounded on two sides by reflective material which serves to increase the light exposure of the sample vessels.

The housing (200) has a plurality of ventilation intrusions (212) which allow air to circulate and cool the sample vessels during irradiation. The housing (200) also has a control panel intrusion (213) in which a control panel may be placed.

EXAMPLE 3

Figure 20:
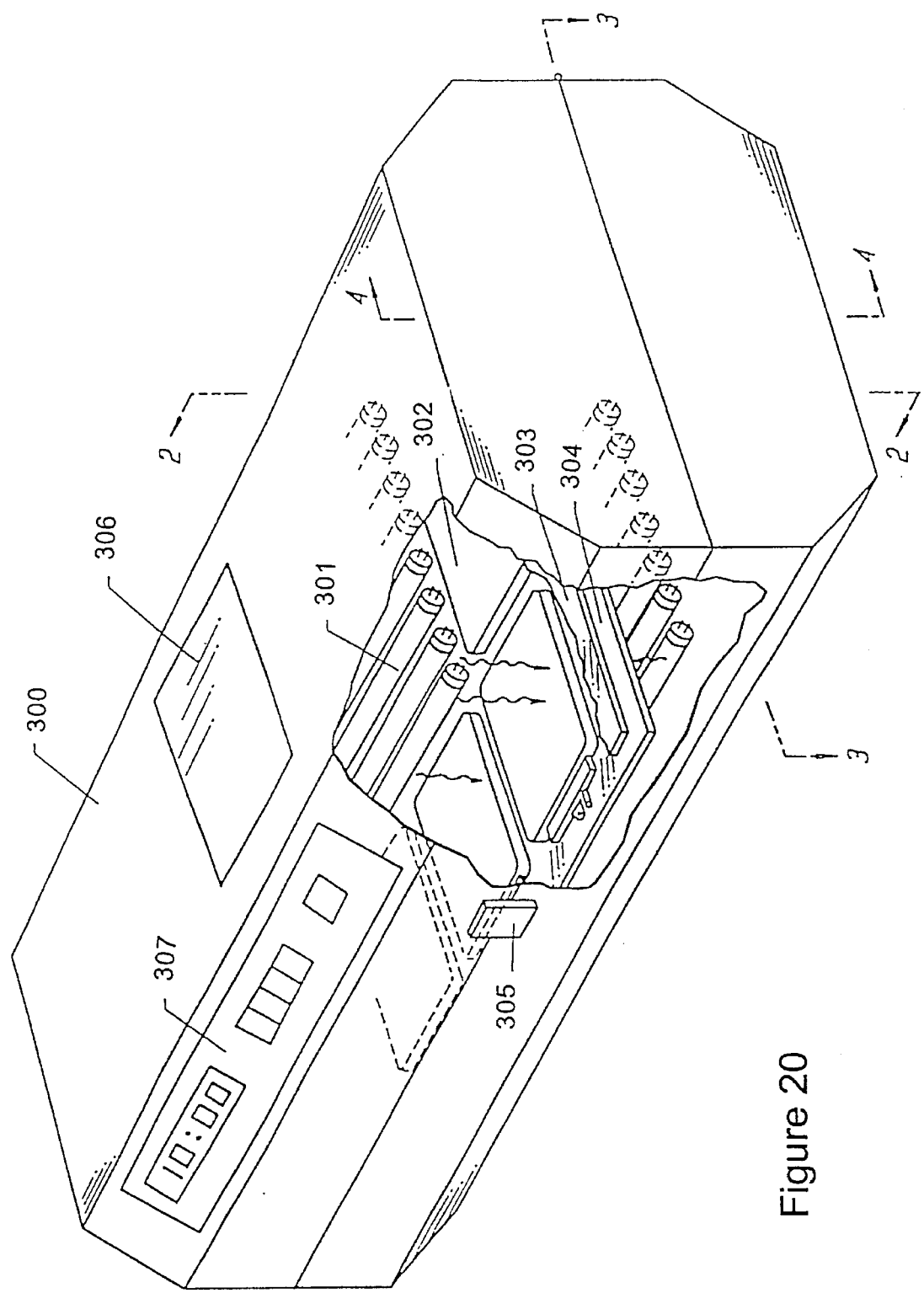
FIG. 20 is a perspective view of one embodiment of the device of the present invention.

FIG. 20 is a perspective view of one embodiment of the device integrating the above-named features. This device is hereinafter referred to as "the Device of Example 3." The figure shows an opaque housing (300) with a portion of it removed, containing an array of bulbs (301) above and below a plurality of representative blood product containing means (302) placed between plate assemblies (303, 304). The plate assemblies (303, 304) are described more fully, subsequently.

The bulbs (301), which are connectable to a power source (not shown), serve as a source of electromagnetic radiation. While not limited to the particular bulb type, the embodiment is configured to accept an industry standard, dual bipin lamp.

The housing (301) can be opened via a latch (305) so that the blood product can be placed appropriately. As shown in FIG. 20, the housing (300), when closed, completely contains the irradiation from the bulbs (301). During irradiation, the user can confirm that the device is operating by looking through a safety viewport (306) which does not allow transmission of ultraviolet light to the user.

The housing (300) also serves as a mount for several electronic components on a control board (307), including, by way of example, a main power switch, a count down timer, and an hour meter. For convenience, the power switch can be wired to the count down timer which in turn is wired in parallel to an hour meter and to the source of the electromagnetic radiation. The count down timer permits a user to preset the irradiation time to a desired level of exposure. The hour meter maintains a record of the total number of radiation hours that are provided by the source of electromagnetic radiation. This feature permits the bulbs (301) to be monitored and changed before their output diminishes below a minimum level necessary for rapid photoactivation.

Figure 21:
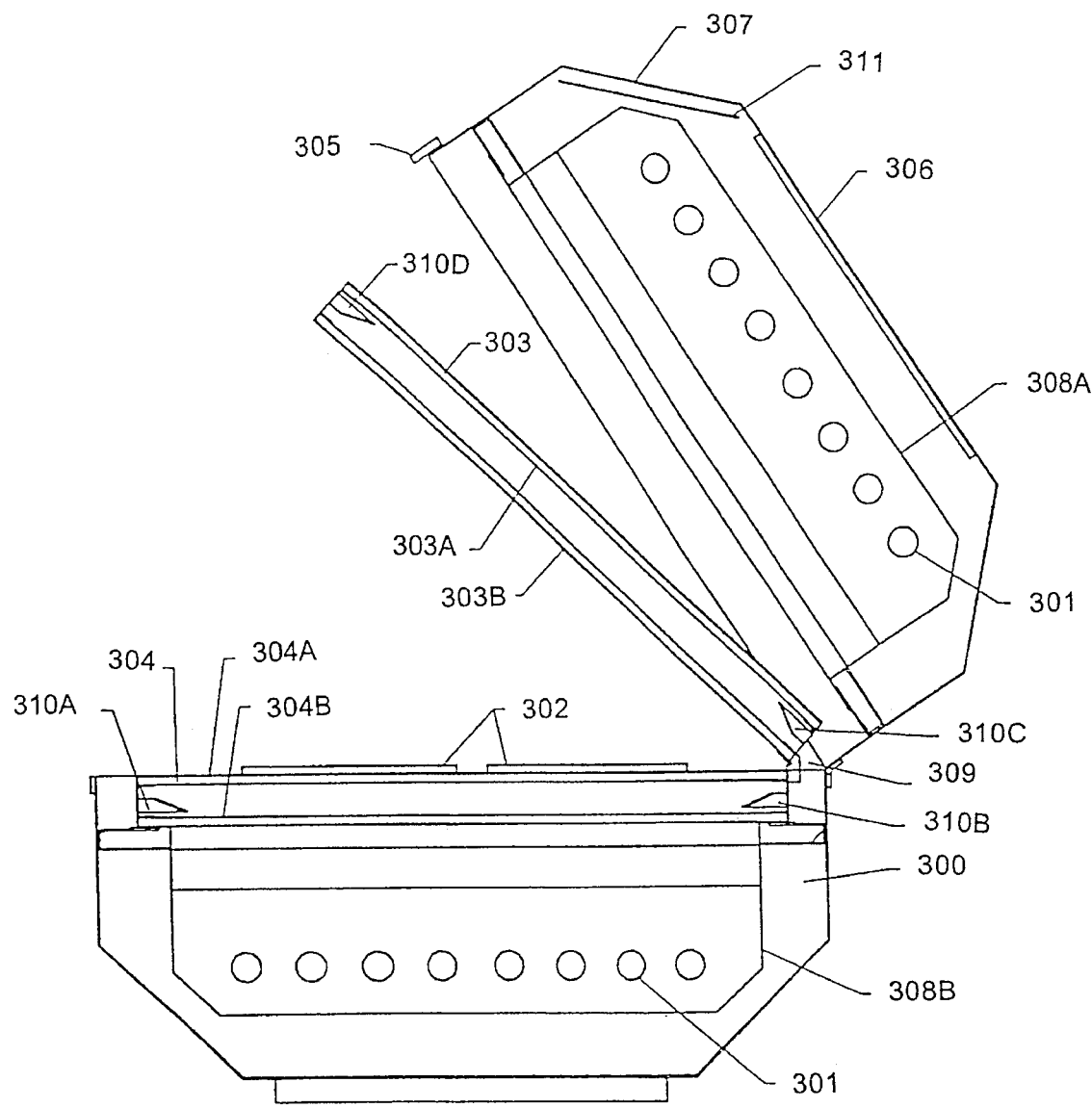
FIG. 21 is a cross-sectional view of the device shown in FIG. 1 along the lines of 2—2.

FIG. 21 is a cross-sectional view of the device shown in FIG. 20 along the lines of 2—2. FIG. 21 shows the arrangement of the bulbs (301) with the housing (300) opened. A reflector (308A, 308B) completely surrounds each array of bulbs (301). Blood product containing means (302) are placed between upper (303) and lower (304) plate assemblies. Each plate assembly is comprised of an upper (303A, 304A) and lower (303B, 304B) plates. The plate assemblies (303, 304) are connected via a hinge (309) which is designed to accommodate the space created by the blood product containing means (302). The upper plate assembly (303) is brought to rest gently on top of the blood product containing means (302) supported by the lower plate (304B) of the lower plate assembly (304).

Detectors (310A, 310B, 310C, 310D) may be conveniently placed between the plates (303A, 303B, 304A, 304B) of the plate assemblies (303, 304). They can be wired to a printed circuit board (311) which in turn is wired to the control board (307).

Figure 22:
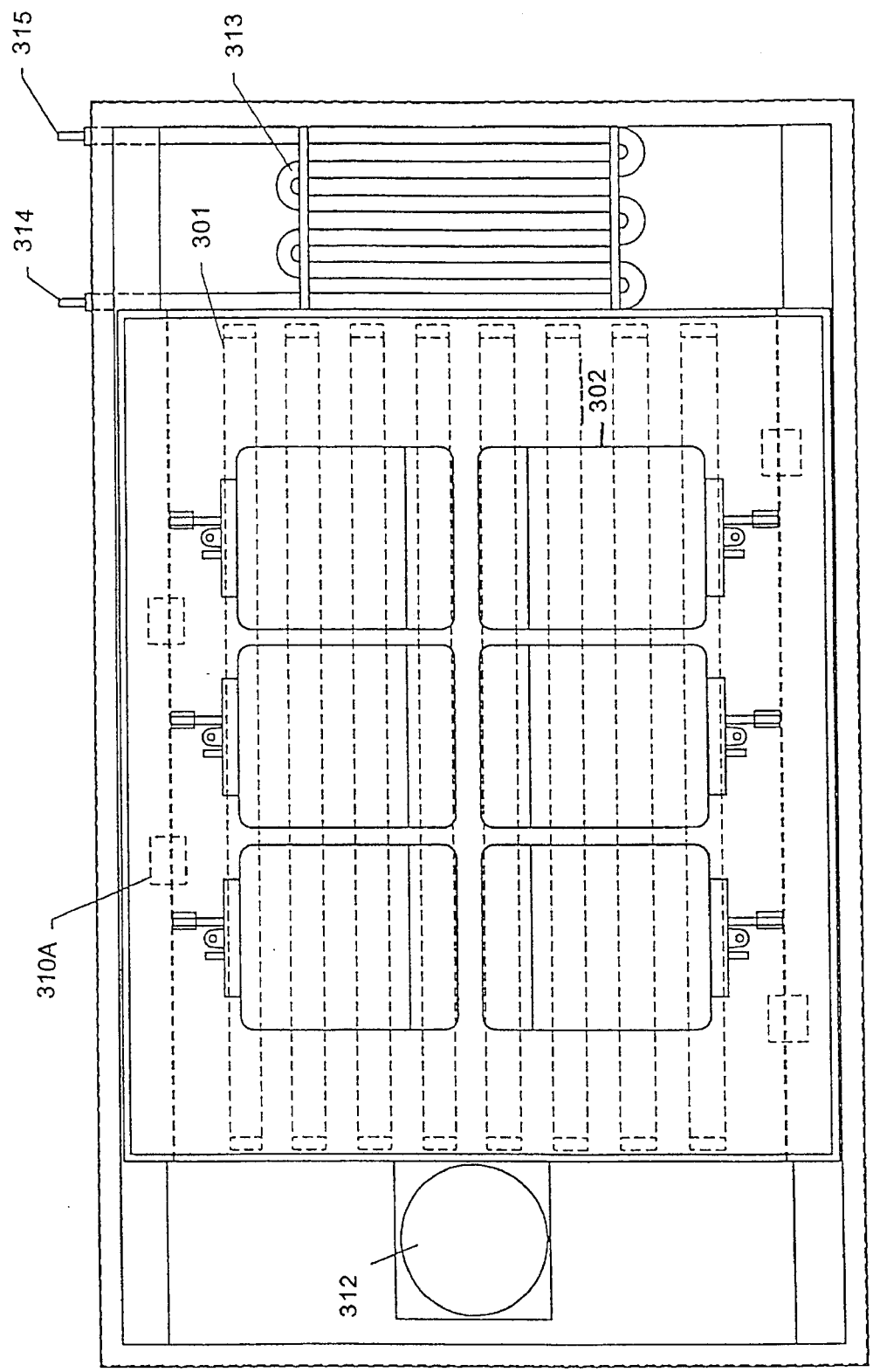
FIG. 22 is a cross-sectional view of the device shown in FIG. 1 along the lines of 3—3.

FIG. 22 is a cross-sectional view of the device shown in FIG. 20 along the lines of 3—3. Six blood product containing means (302) (e.g. teflon platelet unit bags) are placed in a fix relationship above an array of bulbs (301). The temperature of the blood product can be controlled via a fan (312) alone or, more preferably, by employing a heat exchanger (313) having cooling inlet (314) and outlet (315) ports connected to a cooling source (not shown).

Figure 23:
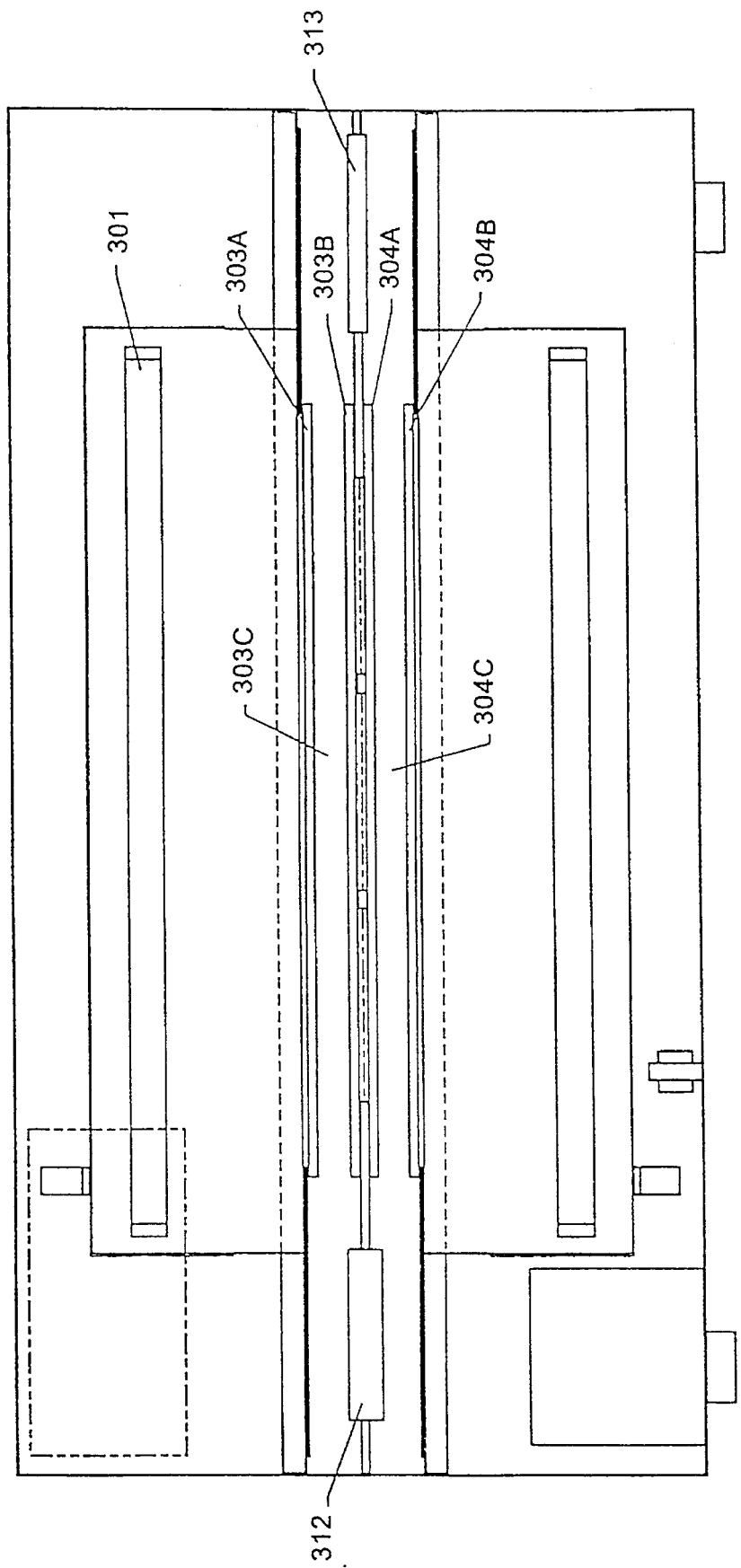
FIG. 23 is a cross-sectional view of the device shown in FIG. 1 along the lines of 4—4.

FIG. 23 is a cross-sectional view of the device shown in FIG. 20 along the lines of 4—4. FIG. 23 more clearly shows the temperature control approach of a preferred embodiment of the device. Upper plate assembly plates (303A, 303B) and lower plate assembly plates (104A, 104B) each create a temperature control chamber (303C, 304C), respectively. The fan (312) can circulate air within and between the chambers (303C, 304C). When the heat exchanger (313) is employed, the circulating air is cooled and passed between the plates (303A, 303B, 304A, 304B).

EXAMPLE 4

Synthesis of
4'-Chloromethyl-8-methoxy-4,5'-dimethylpsoralen

An Intermediate in AMMP Synthesis

This synthesis is shown in FIG. 24. 4,5'-Dimethyl-8-methoxy-psoralen (10 g) (FIG. 24, 1) was dissolved in 500 mL of glacial acetic acid. Chloromethyl methyl ether (50 mL) was added to the above solution at room temperature. After three days the reacted solution was put in an ice-bath until the product crystallized completely. The product was filtered and washed with cold acetic acid to give 4.7 g (39%) white crystals of 4'-chloromethyl-8-methoxy-4,5'-dimethylpsoralen (FIG. 24, 2).

EXAMPLE 5

Synthesis of AMMP

Step 1: 4'-Chloromethyl-8-methoxy-4,5'-dimethylpsoralen (0.15 g) (FIG. 25, 2), 0.33 g of freshly prepared potassium phthalimide (refluxed with acetone for 2 hours, then dried in a vacuum oven at 100° C. for 2 hours) and 20 mL of DMF (dried over 4 Å molecular sieves) were placed in a round bottom flask and stirred overnight at room temperature. The DMF was removed under reduced pressure and the residue was chromatographed (silica gel) with $CHCl_3$. The fractions containing the product were evaporated. The resulting white solid, 8-methoxy-4,5'-dimethyl-4'-(phthalimidomethyl)psoralen (0.2 g)(FIG. 25, 3), was dried in a vacuum oven, then used directly for the next step.

Step 2: 8-methoxy-4,5'-dimethyl-4'-(phthalimidomethyl)psoralen (0.2 g) (FIG. 25, 3), 95% EtOH (45 mL) and 85% aqueous hydrazine hydrate (0.6 mL) were placed in a round bottomed flask with a magnetic stirrer and a thermometer. The mixture was heated at 50° C. until no starting material remained by TLC (95% $CHCl_3$/5% MeOH). The EtOH was removed giving a white solid. $CHCl_3$ (15 mL) and 1 N NaOH (10 mL) were added and the mixture transferred to a separating funnel. The basic solution was further extracted twice with $CHCl_3$, the combined extracts were washed with water, then extracted twice with 0.3 N HCl. The acid extracts were taken to pH~12 with aqueous NaOH solution, then the basic suspension was extracted three times with $CHCl_3$. These combined $CHCl_3$ extracts were washed with water, dried over $Na_2SO_4$, sand the $CHCl_3$ stripped off to give the amine as the free base (white solid). Absolute EtOH was added, then saturated with anhydrous HCl gas. The EtOH was removed and the residue was dried in a vacuum oven to give 0.4 g of light yellow solid, 4'-aminomethyl-4,5'-dimethyl-8-methoxypsoralen hydrochloride salt (AMMP) (FIG. 25, 4).

EXAMPLE 6

Synthesis of a Biotinylated Psoralen

This example describes the synthesis of a biotinilated psoralen that may be used in a filtration system which removes the photoreactive compound from the treated material after the material has been decontaminated.

Step 1: A mixture of 187 mg (0.64 mmole) of 4'-chloromethyl-8-methoxy-4,5'-dimethylpsoralen, from Example 4, and 1.69 g of 1,2-bis-[(2-methylamino)ethoxy]-ethane was refluxed with stirring in 20 mL of dry toluene overnight. The solvent was then stripped off. The residue was acidified by adding 1N HCl, then several drops concentrated HCl to pH~1 and extracted twice with $CHCl_3$. The aqueous layer was made basic with NaOH solution and extracted into $CHCl_3$, washed with $H_2O$, then dried over $Na_2SO_4$. After removal of the solvent, the product was eluted on a silica gel column with $CHCl_3$:EtOH:triethylamine (9:1:0.25). The fractions containing products were combined and the solvent removed giving 0.23 g (83%) of a yellow syrup, 8-methoxy-4,5'-dimethyl-4'-[8-(methylamino)-3,6-dioxaoctylamino)] methylpsoralen.

Step 2: 8-Methoxy-4,5'-dimethyl-4'-[8-(methylamino)-3,6-dioxaoctylamino)]methylpsoralen, 74 mg, was dissolved in 1.6 mL of DMF. Molecular sieves were added, followed by a solution of biotin-amido caproate N-hydroxy succinimide ester (154 mg) in 2 mL of DMF. The reaction mixture was stirred at room temperature under argon. Reaction progress was followed by TLC in (95% $CH_2Cl_2$/5% MeOH). After the reaction was complete, the solvent was stripped off under reduced pressure. The residue was extracted with MeOH. The MeOH was stripped off. The residue was acidified to pH~1 by adding 1N HCl and extracted with $CHCl_3$ about 10 times. The aqueous layer was made basic with NaOH solution pH~12) and extracted into $CHCl_3$, washed with $H_2O$, then dried over $Na_2SO_4$. After removal of the solvent, the free base was dissolved in absolute EtOH, then saturated with HCl gas. The EtOH was removed under vacuum and the solid residue was dried in a vacuum oven to give 5-(biotinamido)pentanoic add N-[N,N'-Dimethyl-3,6-dioxa-N'-(8-methoxy-4,5'-dimethylpsoralen-4'-yl)methyl]-1,8-octanediamine amide ("5B-AMMP"), 96.5 mg.

EXAMPLE 7

Synthesis of Radiolabelled AMMP ([$^3$H]AMMP)

This example describes the synthesis of radiolabeled 4'-aminomethyl-4,5'-dimethyl-8-methoxypsoralen (AMMP).

Step 1: A mixture of 150 mg of 4'-chloromethyl-4,5'-dimethyl-8-methoxypsoralen and water (15 mL) was refluxed with stirring until no starting material was detected by TLC; The resulting suspension was cooled, filtered, rinsed with water and dried to give 4'-hydroxymethyl-8-methoxy-4,5'-dimethylpsoralen (100 mg, 71.5%).

Step 2: 3,5-Dimethylpyrazole (4 g, 43 mmole) was added to a suspension of chromium trioxide (4.25 g, 43 mmole) in methylene chloride (125 mL) and the mixture was stirred at room temperature under argon for 15 minutes. To the resulting dark red solution, 4'-hydroxymethyl-8-methoxy-4, 5'-dimethylpsoralen (4.0 g, 16 mmole) was added in one portion and the reaction mixture was then stirred at room temperature for 2 hours. The solvent was removed and the residue was chromatographed on silica gel with $CH_2Cl_2$. The fractions containing product were combined and the solvent removed giving 4,5'-dimethyl-4'-formyl-8-methoxypsoralen (2.85 g, 71.8%). Further purification was accomplished by recrystallization from 95% EtOH, yielding white crystals.

Step 3: EtOH (2 mL, 95%) was added to 4,5'-dimethyl-4'-formyl-8methoxypsoralen (34 mg, 0.125 mmole). This suspension was added to 25 mCi sodium borohydride (0.042 mmole) ($^3$H, 600 mCi/mmole) and the solution was returned to the initial vial. The borohydride vial was rinsed with 2×1 mL EtOH and the rinses were added to the reaction. The reaction was stirred for 3 hrs and monitored by TLC in chloroform:methanol 98:2. The solvent was removed under a vacuum and the solid residue was dissolved in approximately 1 mL chloroform:methanol 98:2. This was loaded onto a 1 cm×30 cm, 60–200 mesh, silica gel column and eluted with 98:2. The product, 8-methoxy-4,5'-dimethyl-4'-hydroxy[$^3$H]methylpsoralen, was pooled and solvent removed under vacuum. 23 mg (0.084 mmole) was recovered.

Step 4: The 23 mg (0.084 mmole) of 4'-hydroxy[$^3$H] methyl-8-methoxy-4,5'-dimethylpsoralen was dissolved in 2 mL of dry chloroform and stirred under argon. Distilled thionyl chloride (27 µL, 0.38 mmole) was added to this and the reaction mix was stirred under argon for 3 hours. TLC in chloroform showed complete reaction. The recovery was not determined at this point.

Step 5: The 4'-chloro[$^3$H]methyl-8-methoxy-4,5'-dimethylpsoralen (0.042 mmole) was dried and dissolved in 2 mL of distilled DMF. Dry potassium phthalimide (27 mg, 0.147 mmole) was added and the reaction was heated to approximately 40° C. with stirring. After several hours TLC in chloroform showed incomplete reaction. Another 33 mg (0.18 mmole) of potassium phthalimide was added and the reaction was stirred overnight at 40° C. The DMF was removed under vacuum and the solid was dissolved in 1 mL of chloroform:methanol 98:2. This was loaded onto a 1 cm×30 cm, 60–200 mesh, silica gel column and eluted with chloroform:methanol 98:2. The product, 4'-phthalimido[$^3$H] methyl-4,5'-dimethyl-8-methoxypsoralen, was pooled and solvent was removed under vacuum.

Step 6: The 4'-phthalimido [$^3$H]methyl-4,5'-dimethyl-8-methoxypsoralen was dissolved in the 4 mL of 95% EtOH. Hydrazine hydrate (40 ul, 0.6 mmole) was added and the reaction was heated to approximately 50° C. with stirring overnight. TLC in chloroform:methanol 95:5 showed only about 12% reacted. Another 3 mL 95% EtOH was added to try to dissolve everything. A total of 250 µL additional hydrazine was added and reacted overnight again. TLC the next day showed approximately 80% product. The solvent was removed under vacuum. Chloroform (5 mL) and 5 mL 0.1M NaOH was added. Next the chloroform was removed by extraction. Extraction was performed two more times with 5 mL chloroform and the extracts were pooled. Then the chloroform was extracted with 10 mL of 0.1M HCl and the HCl was washed three times with 5 mL of chloroform. The aqueous layer was stripped and the solid was brought up in 10 mL EtOH. Concentrated HCl (10 drops) was added. The product, ([$^3$H]AMMP) was stripped and dissolved in 5 mL of water.

EXAMPLE 8

The nucleic acid binding affinity of AMMP was measured using radiolabeled AMMP with calf thymus DNA in Tris-EDTA buffer. The formation of psoralen:DNA adducts expressed as numbers of psoralen adducts per 1000 base pairs (bp) was measured under identical (equimolar) conditions along with AMT and 8-MOP (FIG. 26).

Each tritium labelled psoralen (1.4 uM) was added to a solution of calf thymus DNA (1.0 uM) then irradiated in the Device of Example 3, above, for the indicated time. Aliquots were removed and precipitated 3 times with EtOH. The binding ratio was calculated from the final DNA concentration (determined by optical density) and the amount of covalently bound psoralen determined by scintillation counting.

Figure 26:
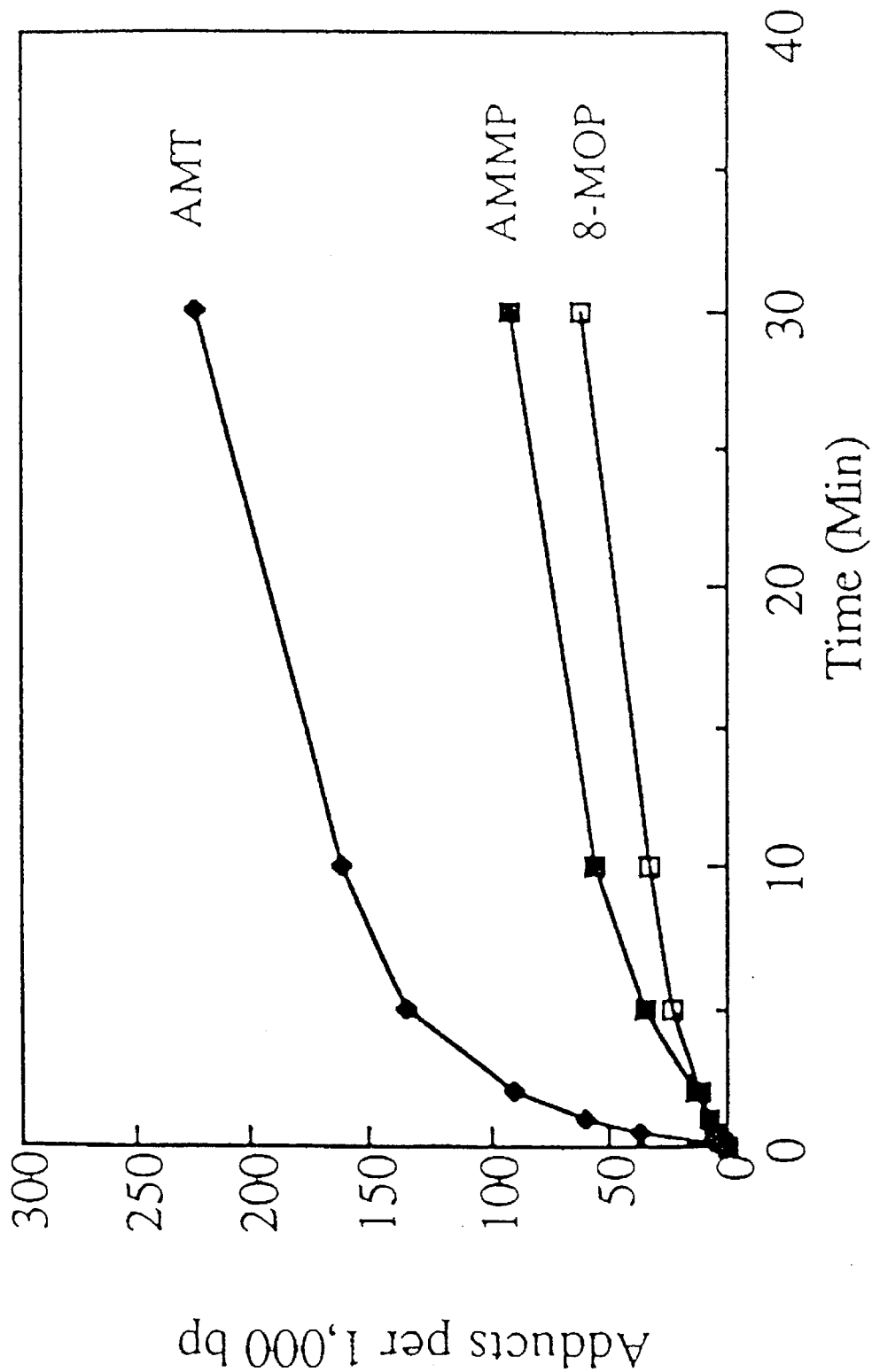
FIG. 26 is a graph showing the photoaddition of 4'-aminomethyl-4,5',8-trimethylpsoralen (AMT), 4'-aminomethyl-4,5'-dimethyl-8-methoxypsoralen (AMMP) and 8-methoxypsoralen (8-MOP) to nucleic acid after exposure to ultraviolet light.

As shown in FIG. 26, AMMP binds approximately twice as well as 8-MOP. AMMP also has a much higher aqueous solubility than 8-MOP, and therefore can provide even higher levels of DNA binding when used at higher concentrations. AMMP also provides significantly higher DNA binding than does 8-MOP at relatively short irradiation times (e.g. 10 minutes), which is an important factor for maintaining platelet function. AMT shows the best binding, forming more than 250 adducts per kilobase pair.

EXAMPLE 9

This example looks at AMT binding of DNA over time for two different photoactivation devices. The example shows that both devices stimulate adequate binding.

The nucleic add binding affinity of AMT was measured using radiolabeled AMT with calf thymus DNA in Tris-EDTA buffer. The formation of psoralen:DNA adducts expressed as numbers of psoralen adducts per 1000 base pairs (bp) was measured.

Tritium labelled AMT (0.83 µg/ul) (118 ul) was added to a solution of calf thymus DNA (600 µg/mL) (2.83 mL) and diluted with 5M NaCl to reach an AMT concentration of 31 µg/mL. 100 ul of the solution was placed in each of 8 glass vials and irradiated for 2, 4, 8, or 16 minutes on either the Device of Example 3 or the Device of Example 2. Aliquots were removed and precipitated 3 times with EtOH. The binding ratio was calculated from the final DNA concentration (determined by optical density) and the amount of covalently bound psoralen determined by scintillation counting.

Figure 27:
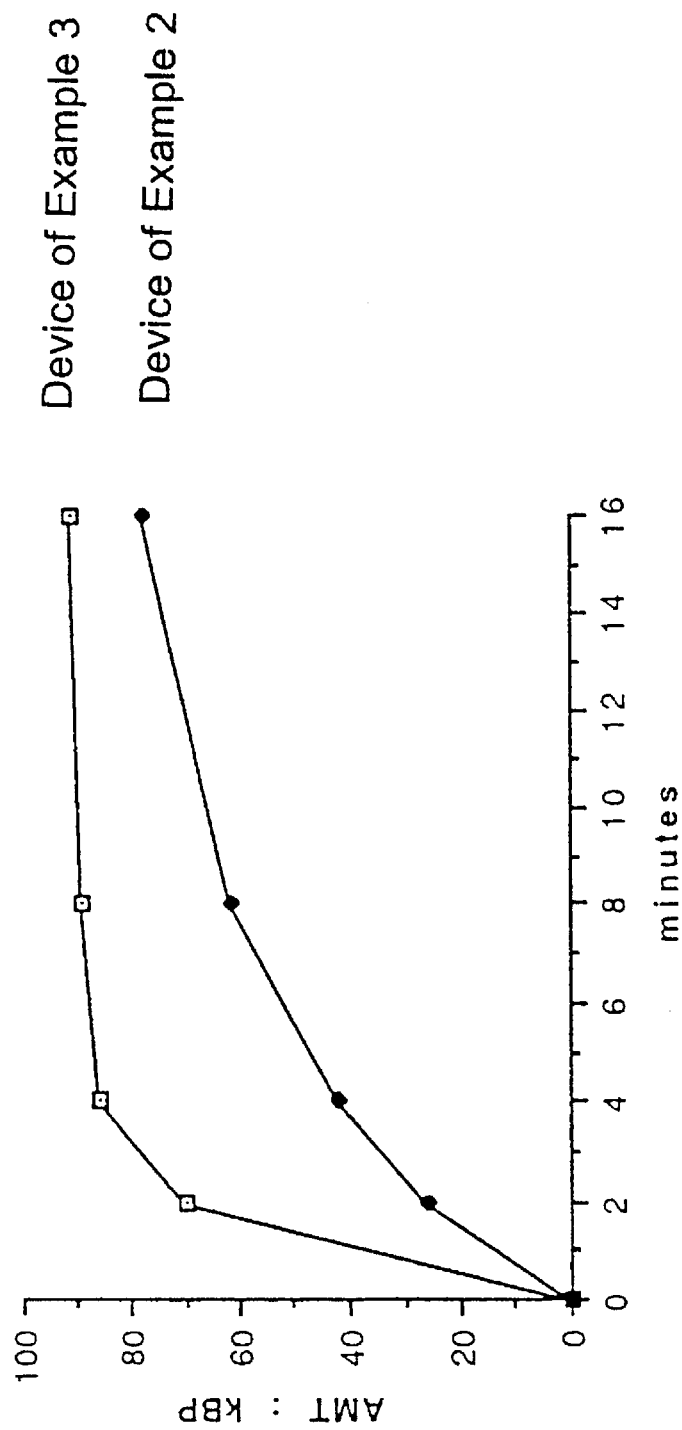
FIG. 27 is a graph showing the photoaddition of 4'-aminomethyl-4,5',8-trimethylpsoralen (AMT) to calf thymus DNA after irradiation with two different photoactivation devices.

As shown in FIG. 27, the Device of Example 3 achieves plateau binding by 4 minutes irradiation, whereas the Device of Example 2 requires longer irradiation time. Irradiation for 16 minutes on the Device of Example 2 causes 77 AMT:DNA adducts per kBP. This is sufficiently close to the plateau binding value of 91 adducts/kBP attained by irradiation on the Device of Example 3 such that the results achieved with the devices can be compared with confidence.

EXAMPLE 10

Pathogen inactivation efficiency was evaluated by examining the ability of AMMP to inactivate cell-associated virus (HIV). Inactivation of cell-associated HIV was performed as follows.

Figure 28:
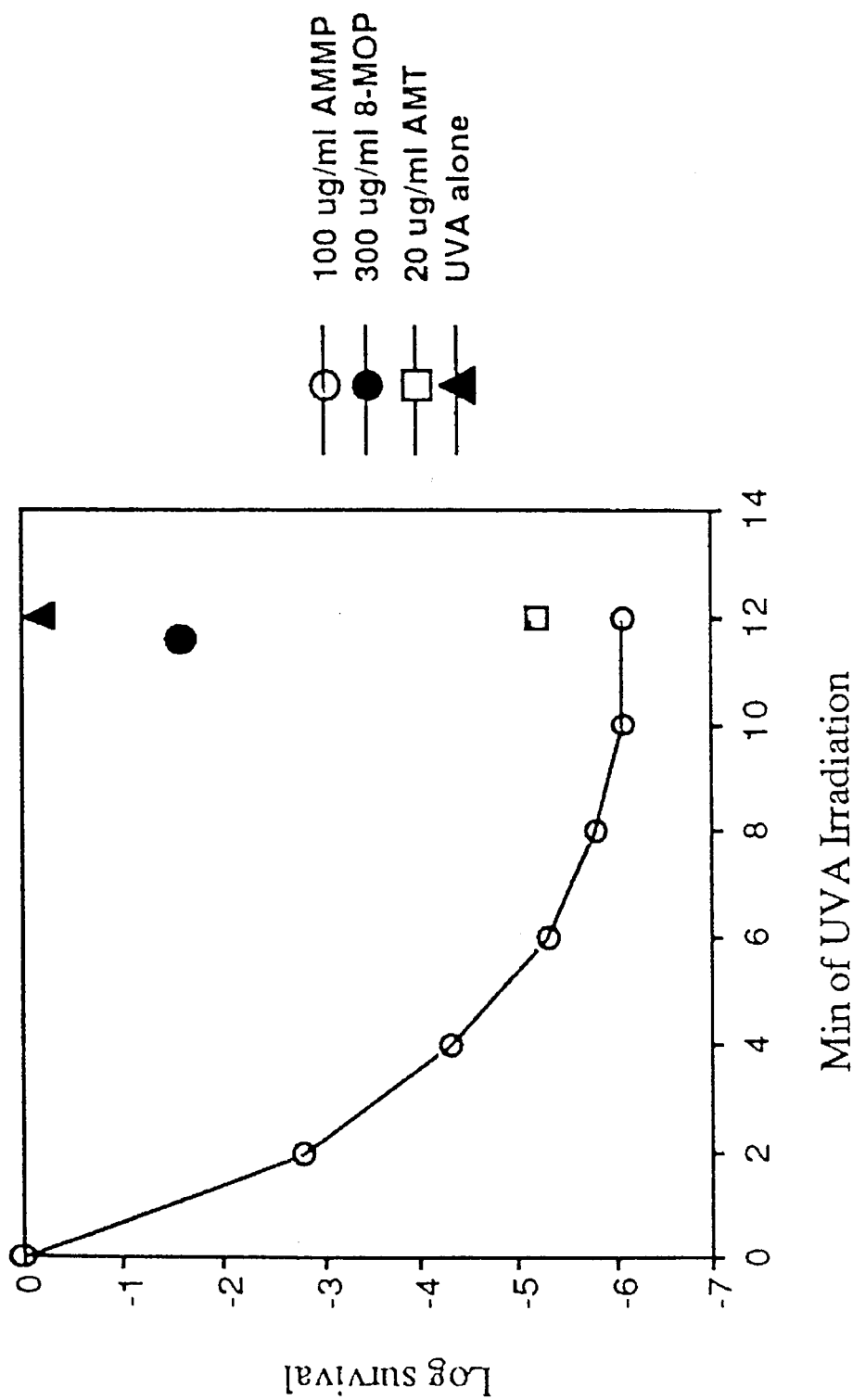
FIG. 28 is a graph showing the viral inactivation of cell-associated HIV by 4'-aminomethyl-4,5',8-trimethylpsoralen (AMT), 4'-aminomethyl-4,5'-dimethyl- 8-methoxypsoralen (AMMP) and 8-methoxypsoralen (8-MOP) after UV irradiation.

H9 cells infected with HIV were added to standard human platelet concentrates ($2.5 \times 10^7$ cells per concentrate), final concentration $5 \times 10^5$ cells per concentrate. Aliquots of HIV contaminated platelet concentrate (5 mL) were placed in Pyrex chambers. The chambers had previously been coated on the inside with silicon. The platelet concentrates were treated with either AMMP (100 μg/mL), 8-MOP (300 μg/mL), or AMT (20 μg/mL) and irradiated with 320–400 nm ($20 mW/cm^2$) for up to 12 min. on a device similar to the Device of Example 3. The photoactivation device used here was previously tested and found to result in light exposure comparable to the Device of Example 3. (Data not shown). Aliquots for measurement of residual HIV infectivity in the AMMP treated sample were withdrawn and cultured after 2, 4, 6, 8, 10, and 12 min. Residual HIV infectivity was assayed using a previously described MT-2 infectivity assay. Hanson, C. V., et al., J. Clin. Micro 28:2030 (1990). The results are shown in FIG. 28.

UVA light alone had no effect, 8-MOP inactivated only 1.2 logs of HIV, while AMT and AMMP markedly reduced the titer of cell-associated HIV. At a concentration of 100 μg/mL, AMMP is substantially more efficient than 8-MOP. AMT appears to be the most efficient. 20 μg/mL AMT reduced the viral titer almost as much as 100 μg/mL AMMP.

EXAMPLE 11

A major concern is whether the decontamination process interferes with the chemistry tests. Clearly, one does not want to inactivate pathogens and render the serum or plasma unusable for testing.

In this experiment, refrigerator-stored patient serum was used from a hospital clinical laboratory. Five patient samples were selected for nineteen (19) of the most common chemistry tests. It was hoped that five patients would provide a wide range of values for these tests. Three nucleic acid binding compounds were evaluated at a single concentration: 8-MOP (320 μg/mL), AMT (20 μg/mL) and 5B-AMMP (40 μg/mL). These concentrations were selected on the basis of effective inactivation of HIV in a culture assay (data not shown).

As controls, the samples were tested i) without any treatment, ii) with UV irradiation only (i.e. no compound), and iii) with solvent only. The latter was performed as a specific control for 8-MOP which was diluted in solvent (EtOH) as a stock to allow for the high working concentration.

A total sample volume of 0.3 mL was selected on the basis of the volume requirements of the Kodak Ectachem Analyzer instrument, Kodak Corp., for the 19 clinical tests. To reach this sample volume, a volume of stock concentrate of each compound was added to the necessary amount of serum in a 1 mL Eppendorf tube. In the case of 8-MOP, 0.015 mL of concentrate was added to 0.285 mL of serum. For AMT, 0.030 mL of concentrate was added to 0.270 mL of serum. For 5B-AMMP, 0.006 mL was added to 0.294 mL of serum.

Irradiation was performed on the HRI-100 device. A single 15 minute irradiation time was used. Given the short irradiation time, the irradiations were performed without cooling of the reaction chamber.

The results are shown in Tables 4–8. The data for each of the five patients is in two sets of tables (A and B): the first shows the results of AMT and 5B-AMMP with relevant controls; the second shows the results with 8-MOP along with the 8-MOP controls. No adjustments in the test values have been made to reflect the dilutions.

Taking into account the dilution factors, the raw data for Patients 1–5 (Tables 4A, 5A, 6A, 7A and 8A) indicates no impact of the treatment on any of the tests that is due to the compounds AMT and 5B-AMMP. However, UV irradiation alone appears to have a significant impact on Uric Acid and Total Bilirubin.

The second set of tables for Patients 1–5 (Tables 4B, 5B, 6B, 7B and 8B) is in marked contrast. Clearly, the small amount of solvent necessary to achieve the requisite high 8-MOP levels produces an unacceptable change in the test values. This is particularly true for potassium values, which are arguably the most important clinical chemistry test to the hospital.

TABLE 4A

| | Patient 1 | | | |
|---|---|---|---|---|
| Tests | Untreated | UV Only | AMT | 5B-AMMP |
| GLUCOSE | 130 | 136 | 121 | 131 |
| SODIUM | 133 | 135 | 121 | 132 |
| POTASSIUM | 4.1 | 4.1 | 3.7 | 4.1 |
| CHLORIDE | 84 | 85 | 75 | 82 |
| $CO_2$ | 36 | 32 | 28 | 32 |
| BUN | 48 | 48 | 43 | 46 |
| CREAT | 1.9 | 2.0 | 1.8 | 1.9 |
| TOTAL | 6.6 | 6.7 | 6.2 | 6.6 |
| ALBUMIN | 3.6 | 3.8 | 3.4 | 3.8 |
| CALCIUM | 9.8 | 10.2 | 9.2 | 9.9 |
| PHOS ACID | 2.9 | 3.0 | 2.7 | 2.9 |
| URIC ACID | 13.6 | 12.1 | 9.9 | 10.9 |
| BILIRUBIN | 1.7 | 0.9 | 0.9 | 0.9 |
| AMYLASE | 79 | 85 | 65 | 72 |
| ALK PHOS | 166 | 174 | 156 | 167 |
| ALT | 44 | 35 | 30 | 34 |
| AST | 121 | 115 | 110 | 121 |
| LDH | 157 | 156 | 141 | 153 |
| CPK | 33 | 31 | 30 | 30 |

TABLE 4B

| | Patient 1 | | | |
|---|---|---|---|---|
| Tests | Untreated | UV Only | 8-Mop | 5B-AMMP |
| GLUCOSE | 130 | 136 | 120 | 125 |
| SODIUM | 133 | 135 | 154 | 153 |
| POTASSIUM | 4.1 | 4.1 | 5.6 | 5.4 |
| CHLORIDE | 84 | 85 | 89 | 90 |
| $CO_2$ | 36 | 32 | 24 | 23 |
| BUN | 48 | 48 | 50 | 51 |
| CREAT | 1.9 | 2.0 | 2.0 | 2.1 |
| TOTAL PROTEIN | 6.6 | 6.7 | 6.5 | 6.7 |
| ALBUMIN | 3.6 | 3.8 | 3.6 | 3.8 |
| CALCIUM | 9.8 | 10.2 | 10.2 | 10.4 |
| PHOS ACID | 2.9 | 3.0 | 2.9 | 2.8 |
| URIC ACID | 13.6 | 12.1 | 9.2 | 11.3 |
| BILIRUBIN | 1.7 | 0.9 | 0.9 | 0.8 |
| AMYLASE | 79 | 85 | 61 | 66 |
| ALK PHOS | 166 | 174 | 155 | 157 |
| ALT | 44 | 35 | 9 | 28 |
| AST | 121 | 115 | 84 | 95 |
| LDH | 157 | 156 | 152 | 166 |
| CPK | 33 | 31 | 29 | 29 |

TABLE 5A

| | Patient 2 | | | |
|---|---|---|---|---|
| Tests | Untreated | UV Only | AMT | 5B-AMMP |
| GLUCOSE | 114 | 118 | 105 | 113 |
| SODIUM | 136 | 138 | 123 | 134 |
| POTASSIUM | 4.4 | 4.4 | 4.0 | 4.3 |
| CHLORIDE | 96 | 97 | 86 | 95 |
| $CO_2$ | 20 | 19 | 16 | 20 |
| BUN | 6 | 6 | 5 | 6 |

TABLE 5A-continued

Patient 2

| Tests | Untreated | UV Only | AMT | 5B-AMMP |
|---|---|---|---|---|
| CREAT | 1.3 | 1.4 | 1.3 | 1.3 |
| TOTAL PROTEIN | 7.5 | 7.5 | 7.0 | 7.5 |
| ALBUMIN | 4.2 | 4.4 | 3.9 | 4.2 |
| CALCIUM | 10.0 | 10.4 | 9.4 | 10.2 |
| PHOS ACID | 3.5 | 3.5 | 3.1 | 3.4 |
| URIC ACID | 5.5 | 4.5 | 3.4 | 4.1 |
| BILIRUBIN | 1.0 | 0.6 | 0.6 | 0.7 |
| AMYLASE | 49 | <48 | <48 | <48 |
| ALK PHOS | 85 | 85 | 76 | 81 |
| ALT | 23 | 21 | 16 | 18 |
| AST | 21 | 19 | 20 | 19 |
| LDH | 173 | 169 | 150 | 168 |
| CPK | 71 | 64 | 60 | 63 |

TABLE 5B

Patient 2

| Tests | Untreated | UV Only | 8-Mop | Ethanol |
|---|---|---|---|---|
| GLUCOSE | 114 | 118 | 105 | 107 |
| SODIUM | 136 | 138 | 156 | 156 |
| POTASSIUM | 4.4 | 4.4 | 5.8 | 5.8 |
| CHOLORIDE | 96 | 97 | 101 | 104 |
| $CO_2$ | 20 | 19 | 14 | 15 |
| BUN | 6 | 6 | 7 | 7 |
| CREAT | 1.3 | 1.4 | 1.4 | 1.5 |
| TOTAL PROTEIN | 7.5 | 7.5 | 7.5 | 7.5 |
| ALBUMIN | 4.2 | 4.4 | 4.2 | 4.3 |
| CALCIUM | 10.0 | 10.4 | 10.3 | 10.5 |
| PHOS ACID | 3.5 | 3.5 | 3.4 | 3.4 |
| URIC ACID | 5.5 | 4.5 | 3.2 | 4.2 |
| BILIRUBIN | 1.0 | 0.6 | 0.7 | 0.7 |
| AMYLASE | 49 | <48 | <48 | 66 |
| ALK PHOS | 85 | 85 | 82 | 81 |
| ALT | 23 | 21 | 1 | 19 |
| AST | 21 | 19 | <2 | 25 |
| LDH | 173 | 169 | 162 | 175 |
| CPK | 71 | 64 | 59 | 57 |

TABLE 6A

Patient 3

| Tests | Untreated | UV Only | AMT | 5B-AMMP |
|---|---|---|---|---|
| GLUCOSE | 86 | 89 | 79 | 87 |
| SODIUM | 141 | 142 | 127 | 138 |
| POTASSIUM | 4.7 | 4.7 | 4.3 | 4.6 |
| CHLORIDE | 101 | 103 | 92 | 100 |
| $CO_2$ | 29 | 25 | 24 | 26 |
| BUN | 19 | 20 | 17 | 19 |
| CREAT | 1.2 | 1.2 | 1.2 | 1.2 |
| TOTAL PROTEIN | 7.1 | 7.3 | 6.5 | 7.1 |
| ALBUMIN | 4.4 | 4.5 | 4.0 | 4.4 |
| CALCIUM | 9.9 | 10.2 | 9.2 | 10.0 |
| PHOS ACID | 4.1 | 4.2 | 3.8 | 4.1 |
| URIC ACID | 4.7 | 3.4 | 2.9 | 2.7 |
| BILIRUBIN | 0.6 | 0.3 | 0.3 | 0.3 |
| AMYLASE | 83 | 87 | 70 | 79 |
| ALK PHOS | 45 | 44 | 40 | 42 |
| ALT | 30 | 30 | 28 | 23 |
| AST | 33 | 26 | 26 | 27 |
| LDH | 97 | 96 | 86 | 93 |
| CPK | 51 | 48 | 45 | 48 |

TABLE 6B

Patient 3

| Tests | Untreated | UV Only | 8-Mop | Ethanol |
|---|---|---|---|---|
| GLUCOSE | 86 | 89 | 80 | 81 |
| SODIUM | 141 | 142 | 159 | 162 |
| POTASSIUM | 4.7 | 4.7 | 6.2 | 6.2 |
| CHLORIDE | 101 | 103 | 107 | 110 |
| $CO_2$ | 29 | 25 | 22 | 18 |
| BUN | 19 | 20 | 21 | 21 |
| CREAT | 1.2 | 1.2 | 1.3 | 1.4 |
| TOTAL PROTEIN | 7.1 | 7.3 | 7.0 | 7.1 |
| ALBUMIN | 4.4 | 4.5 | 4.2 | 4.3 |
| CALCIUM | 9.9 | 10.2 | 10.1 | 10.2 |
| PHOS ACID | 4.1 | 4.2 | 4.1 | 4.0 |
| URIC ACID | 4.7 | 3.4 | 2.3 | 2.8 |
| BILIRUBIN | 0.6 | 0.3 | 0.4 | 0.1 |
| AMYLASE | 83 | 87 | 72 | 74 |
| ALK PHOS | 45 | 44 | 41 | 41 |
| ALT | 30 | 30 | 4 | 24 |
| AST | 33 | 26 | 4 | 25 |
| LDH | 97 | 96 | 96 | 101 |
| CPK | 51 | 48 | 44 | 44 |

TABLE 7A

Patient 4

| Tests | Untreated | UV Only | AMT | 5B-AMMP |
|---|---|---|---|---|
| GLUCOSE | 165 | 172 | 151 | 167 |
| SODIUM | 138 | 138 | 125 | 135 |
| POTASSIUM | 5.8 | 5.8 | 5.3 | 5.7 |
| CHLORIDE | 95 | 96 | 86 | 93 |
| $CO_2$ | 29 | 26 | 23 | 26 |
| BUN | 69 | 68 | 60 | 66 |
| CREAT | 2.4 | 2.4 | 2.3 | 2.4 |
| TOTAL PROTEIN | 6.1 | 6.1 | 5.5 | 5.9 |
| ALBUMIN | 3.4 | 3.5 | 3.1 | 3.4 |
| CALCIUM | 9.1 | 9.4 | 8.5 | 9.1 |
| PHOS ACID | 3.4 | 3.4 | 3.1 | 3.3 |
| URIC ACID | 10.2 | 8.8 | 6.9 | 7.6 |
| BILIRUBIN | 1.9 | 0.8 | 0.9 | 1.0 |
| AMYLASE | <48 | <48 | <48 | <48 |
| ALK PHOS | 78 | 77 | 70 | 77 |
| ALT | 20 | 16 | 15 | 15 |
| AST | 19 | 22 | 21 | 23 |
| LDH | 240 | 231 | 209 | 231 |
| CPK | 82 | 76 | 70 | 75 |

TABLE 7B

Patient 4

| Tests | Untreated | UV Only | 8-MOP | Ethanol |
|---|---|---|---|---|
| GLUCOSE | 165 | 172 | 151 | 157 |
| SODIUM | 138 | 138 | 156 | 159 |
| POTASSIUM | 5.8 | 5.8 | 7.9 | 7.5 |
| CHLORIDE | 95 | 96 | 99 | 102 |
| $CO_2$ | 29 | 26 | 21 | 18 |
| BUN | 69 | 68 | 69 | 71 |
| CREAT | 2.4 | 2.4 | 2.5 | 2.5 |
| TOTAL PROTEIN | 6.1 | 6.1 | 6.0 | 6.1 |
| ALBUMIN | 3.4 | 3.5 | 3.4 | 3.5 |
| CALCIUM | 9.1 | 9.4 | 9.4 | 9.7 |
| PHOS ACID | 3.4 | 3.4 | 3.4 | 3.3 |
| URIC ACID | 10.2 | 8.8 | 6.6 | 8.1 |
| BILIRUBIN | 1.9 | 0.8 | 0.9 | 0.8 |
| AMYLASE | <48 | <48 | <48 | <48 |
| ALK PHOS | 78 | 77 | 70 | 72 |
| ALT | 20 | 16 | <2 | 13 |
| AST | 19 | 22 | −1 | 15 |
| LDH | 240 | 231 | 230 | 243 |
| CPK | 82 | 76 | 67 | 67 |

TABLE 8A

| Tests | Patient 5 | | | |
|---|---|---|---|---|
| | Untreated | UV Only | AMT | 5B-AMMP |
| GLUCOSE | 83 | 85 | 75 | 83 |
| SODIUM | 141 | 143 | 128 | 139 |
| POTASSIUM | 4.8 | 4.6 | 4.2 | 4.6 |
| CHLORIDE | 105 | 106 | 95 | 103 |
| $CO_2$ | 24 | 23 | 181 | 22 |
| BUN | 18 | 18 | 16 | 17 |
| CREAT | 1.0 | 1.0 | 1.0 | 1.1 |
| TOTAL PROTEIN | 7.5 | 7.5 | 6.9 | 7.4 |
| ALBUMIN | 4.7 | 4.7 | 4.0 | 4.5 |
| CALCIUM | 9.9 | 10.4 | 9.3 | 9.9 |
| PHOS ACID | 3.8 | 3.8 | 3.4 | 3.7 |
| URIC ACID | 7.0 | 5.9 | 4.5 | 4.6 |
| BILIRUBIN | 0.8 | 0.4 | 0.4 | 0.5 |
| AMYLASE | 110 | 105 | 87 | 99 |
| ALK PHOS | 44 | 46 | 41 | 44 |
| ALT | 20 | 17 | 17 | 17 |
| AST | 26 | 21 | 25 | 23 |
| LDH | 137 | 134 | 120 | 128 |
| CPK | 127 | 114 | 108 | 111 |

TABLE 8B

| Tests | Patient 5 | | | |
|---|---|---|---|---|
| | Untreated | UV Only | 8-Mop | Ethanol |
| GLUCOSE | 83 | 85 | 77 | 79 |
| SODIUM | 141 | 143 | 160 | 162 |
| POTASSIUM | 4.8 | 4.6 | 6.0 | 6.1 |
| CHLORIDE | 105 | 106 | 110 | 113 |
| $CO_2$ | 24 | 23 | 18 | 17 |
| BUN | 18 | 18 | 19 | 20 |
| CREAT | 1.0 | 1.0 | 1.2 | 1.3 |
| TOTAL PROTEIN | 7.5 | 7.5 | 7.3 | 7.5 |
| ALBUMIN | 4.7 | 4.7 | 4.3 | 4.6 |
| CALCIUM | 9.9 | 10.4 | 10.2 | 10.5 |
| PHOS ACID | 3.8 | 3.8 | 3.7 | 3.7 |
| URIC ACID | 7.0 | 5.9 | 3.9 | 5.6 |
| BILIRUBIN | 0.8 | 0.4 | 0.6 | |
| AMYLASE | 110 | 105 | 82 | 99 |
| ALK PHOS | 44 | 46 | 46 | 44 |
| ALT | 20 | 17 | −1 | 20 |
| AST | 26 | 21 | 14 | 17 |
| LDH | 137 | 134 | 130 | 139 |
| CPK | 127 | 114 | 106 | 106 |

EXAMPLE 12

Example 11 indicated that the most significant issue is presented by the irradiation process. A second experiment was therefore performed without any compounds to evaluate this question. Again, stored patient serum was used. Two patient samples were selected for testing Uric Acid and Total Bilirubin. One sample was taken that, upon visual inspection, appeared to have a slightly elevated bilirubin. The other sample appeared to have a normal bilirubin.

The samples were tested i) without any treatment, and ii) with UV irradiation only (i.e. no compound) at three time points (5, 10 and 15 minutes). It was hoped that the impact of UV might be insignificant at shorter irradiation times.

A total sample volume of 0.5 mL was selected for convenience. Since no compounds were used, one need not consider any dilution factors. Irradiation was again performed on the HRI-100 device. Again, the irradiations were performed without cooling of the reaction chamber.

Figure 29:
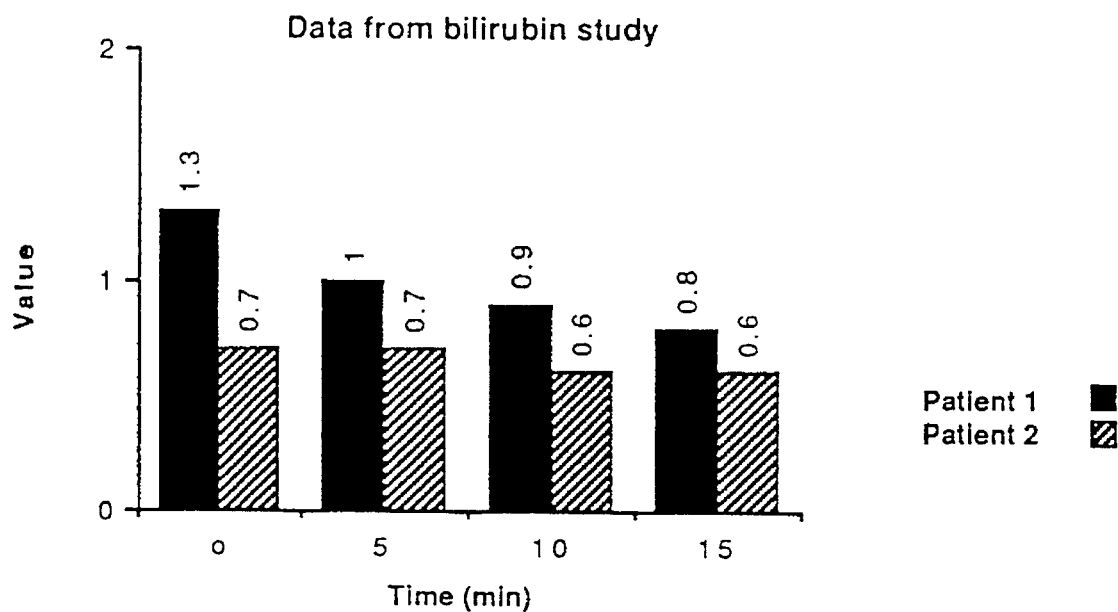
FIG. 29 is a bar graph showing the clinical testing results for Total Bilirubin following the decontamination of human serum according to the present invention.
Figure 30:
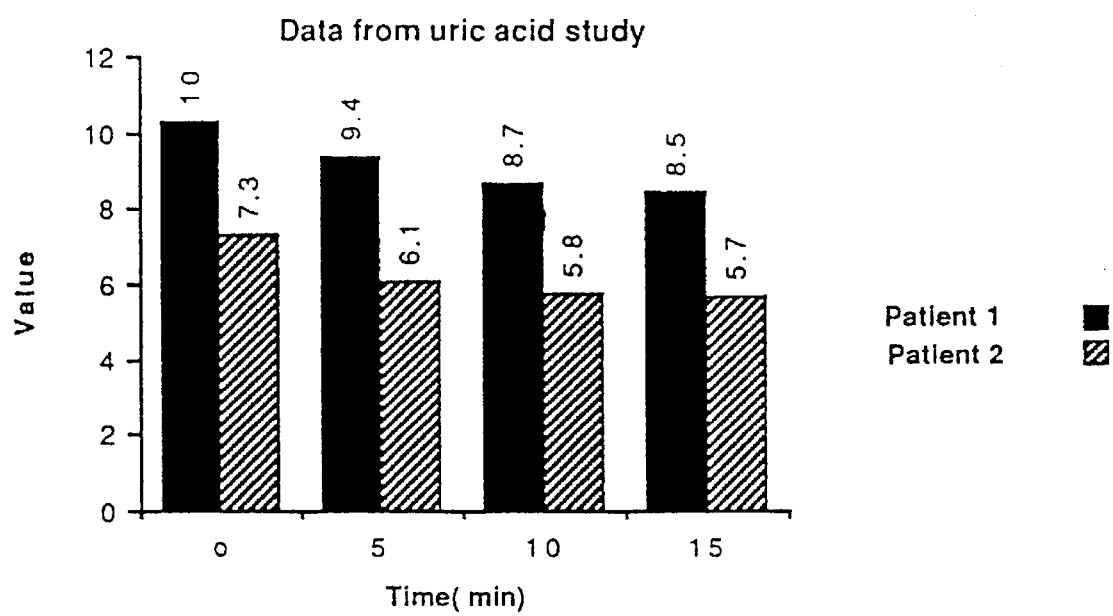
FIG. 30 is a bar graph showing the clinical testing results for Uric Acid following the decontamination of human serum according to the present invention.

The data is shown in two bar graphs: FIG. 29 is a bar graph showing the clinical chemistry testing results for Total Bilirubin; FIG. 30 is a bar graph showing the clinical chemistry testing results for Uric Acid. The values for both patients are shown side by side.

The data confirms that light reduces the value on both of these tests. Interestingly, the reduction is not as apparent in the normal bilirubin range of approximately 0.7. At the higher value of 1.3, however, a fifteen minute (15) irradiation reduces the value by approximately 40%.

EXAMPLE 13

The reduction in Total Bilirubin and Uric Acid values in Example 12 may be due to absorption by these analytes of higher wavelengths than those needed to activate psoralens. This offers the opportunity to filter out these wavelengths without impairing the inactivation significantly.

In this example, experiments were performed using wavelength filters in the HRI-100 device. Specifically, an aqueous solution of $Co(No_3)_2$ was used in combination with $NiSO_4$ to substantially remove the 365 nm component of the emission spectrum of the light source employed. The Co—Ni solution can be conveniently used in place of water as a coolant during the irradiation.

Following an irradiation time course with the filter in place, human serum was assayed for two clinical chemistry tests, bilirubin and uric acid, using the Kodak Ectachem Analyzer. This test was performed to ensure that by using filtered ultraviolet light, bloodborne pathogens can be inactivated while avoiding damage to the serum analytes.

Two patient samples were selected for testing Uric Acid and Total Bilirubin. One sample appeared to have a normal bilirubin upon visual inspection ("Patient 1"). The other appeared to have an extremely high bilirubin level ("Patient 2").

A total sample volume of 0.2 mL was selected for convenience. No compounds were used. Irradiation was performed on the HRI-100 device with and without the liquid filter in the sample trough. The data is shown in Table 9, below. The values for both Uric Acid (UA) and Total Bilirubin (TB) are shown side by side.

TABLE 9

| | Unfiltered | | | | | Filtered | | | |
|---|---|---|---|---|---|---|---|---|---|
| | 0 | 5 | 10 | 15 | 30 | 5 | 10 | 15 | 30 |
| Filter Experiments: Patient 1 | | | | | | | | | |
| UA | 5.7 | 5.4 | 5.1 | 4.8 | 4.4 | 5.7 | 5.6 | 5.6 | 5.6 |
| TB | 1.8 | 1.4 | 1.2 | 1.0 | 0.7 | 1.8 | 1.7 | 1.7 | 1.6 |
| Filter Experiments: Patient 2 | | | | | | | | | |
| UA | 2.6 | 2.5 | 2.4 | 2.3 | 2.2 | 2.6 | 2.6 | 2.5 | 2.5 |
| TB | 21 | 19 | 17 | 16 | 14 | 21 | 21 | 21 | 19 |

The data is clear. Even with an extremely elevated bilirubin (see Patient 2 results), the filter is able to avoid any significant reduction in the value out to 30 minutes of irradiation.

EXAMPLE 14

In Example 13, it was demonstrated that the reduction in Uric Acid and Total Bilirubin could be avoided under conditions where certain wavelengths were filtered. In this example, it is demonstrated that this filtering does not impair the inactivation process.

The binding of AMT to calf thymus DNA was studied using the HRI-100 and a liquid filter solution that transmits only a specific region of the electromagnetic spectrum. An aqueous solution of $Co(No_3)_2$ and $NiSO_4$ to remove the 365 nm component of the emission spectrum of the fluorescent source of the HRI-100. This reduced intensity approximately 40 fold.

The results are shown in Table 10. Clearly, AMT binding using the filter is reduced but adequate; while intensity was reduced 40 fold, binding was reduced only 6 fold. A fifteen minute irradiation will provide the requisite level of psoralen addition to the DNA to inactivate all pathogens.

TABLE 10

| TIME | RAW COUNTS (CMP) | | ADDUCTS per 1000 BP | |
|---|---|---|---|---|
| (min) | Unfiltered | Filtered | Unfiltered | Filtered |
| 0 | 124 | 176 | .26 | .68 |
| 1 | 17008 | 4558 | 44 | 9.54 |
| 2 | 23294 | 8364 | 60.5 | 17.04 |
| 5 | 27754 | 14352 | 71.5 | 36.75 |
| 10 | 28752 | 21024 | 74 | 54.5 |
| 15 | 30648 | 24418 | 79.25 | 63 |
| 30 | — | 28402 | — | 73.25 |

EXAMPLE 15

Example 14 examined the effect of filtering on binding. The results demonstrated that although filtering the UV light lowers intensity 40 fold, it only reduces binding of AMT 6 fold. This example addresses the issue of how filtering the UV light effects the inactivation process when using AMT and AMMP.

This example presents data on AMT and AMMP inactivation of cell-free HIV in serum and in culture media. HIV-infected H9 cells were seeded into human serum or synthetic medium. Aliquots of medium were placed in Pyrex chambers, described in Example 10, and AMT was added to a concentration of 20 µg/mL AMT. Some samples were irradiated unfiltered with 320–400 nm (20mW/cm$^2$) using the irradiation device used in Example 10, for 5, 10 or 15 minutes. Others were irradiated for 15, 30, or 60 minutes with UV filtered with a liquid solution that transmits only a specific region of the electromagnetic spectrum. An aqueous solution of $Co(NO_3)_2$ and $NiSO_4$ removed the 365 nm component of the emission spectrum of the fluorescent light source.

Aliquots of serum were also placed in pyrex chambers and treated with either AMT (20 µg/mL) or AMMP (100 µg/mL). Samples were then irradiated with either filtered or unfiltered light, as described above, for 0.25, 0.5, 1, 2, or 4 minutes.

Control containers of serum and of medium were treated with UVA light alone. Controls for each concentration of AMT and AMMP were not irradiated. Residual HIV infectivity was assayed using a previously described MT-2 infectivity assay. Hanson, C. V., J. Clin. Micro 28:2030 (1990).

Figure 31:
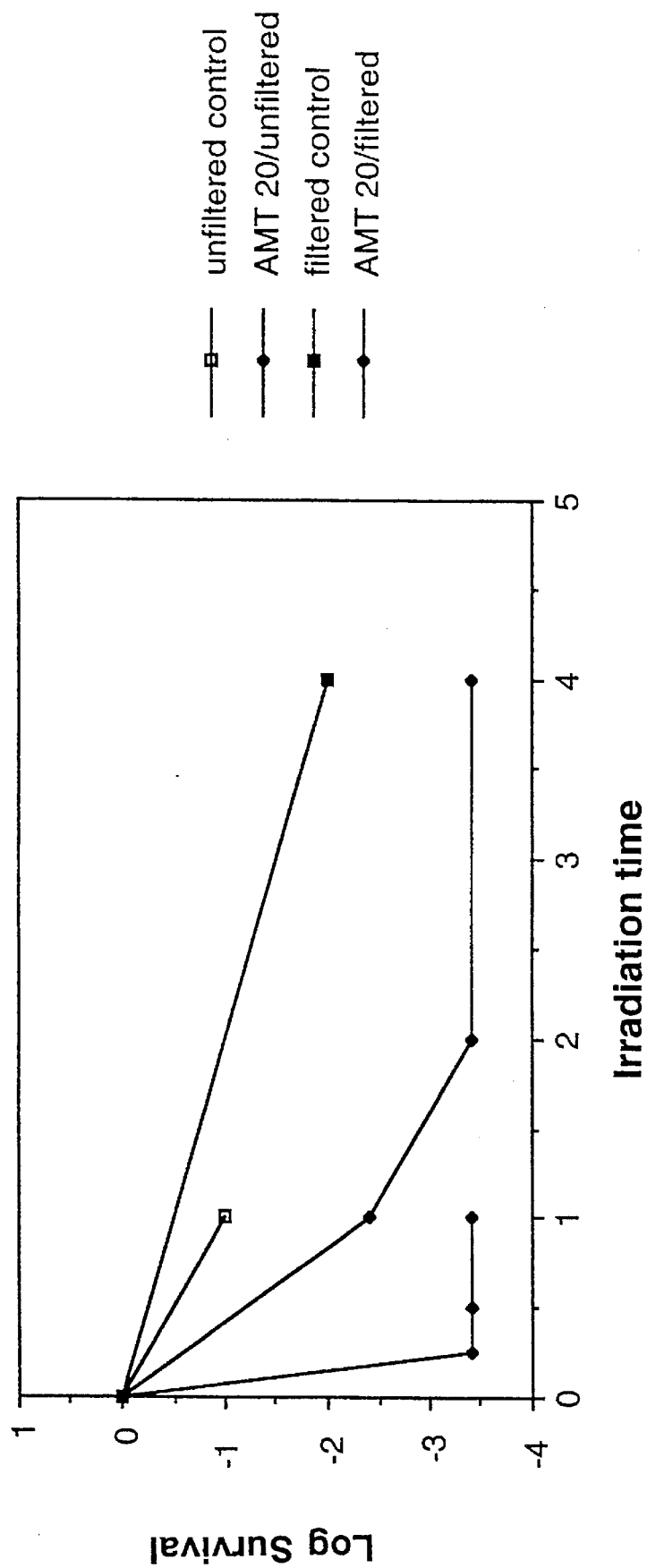
FIG. 31 is a graph showing the viral inactivation of cell-associated HIV in medium by 4'-aminomethyl-4,5',8-trimethylpsoralen (AMT) when irradiated with and without a liquid filter providing wavelength cutoffs at 320 nm and at 360 nm.
Figure 32:
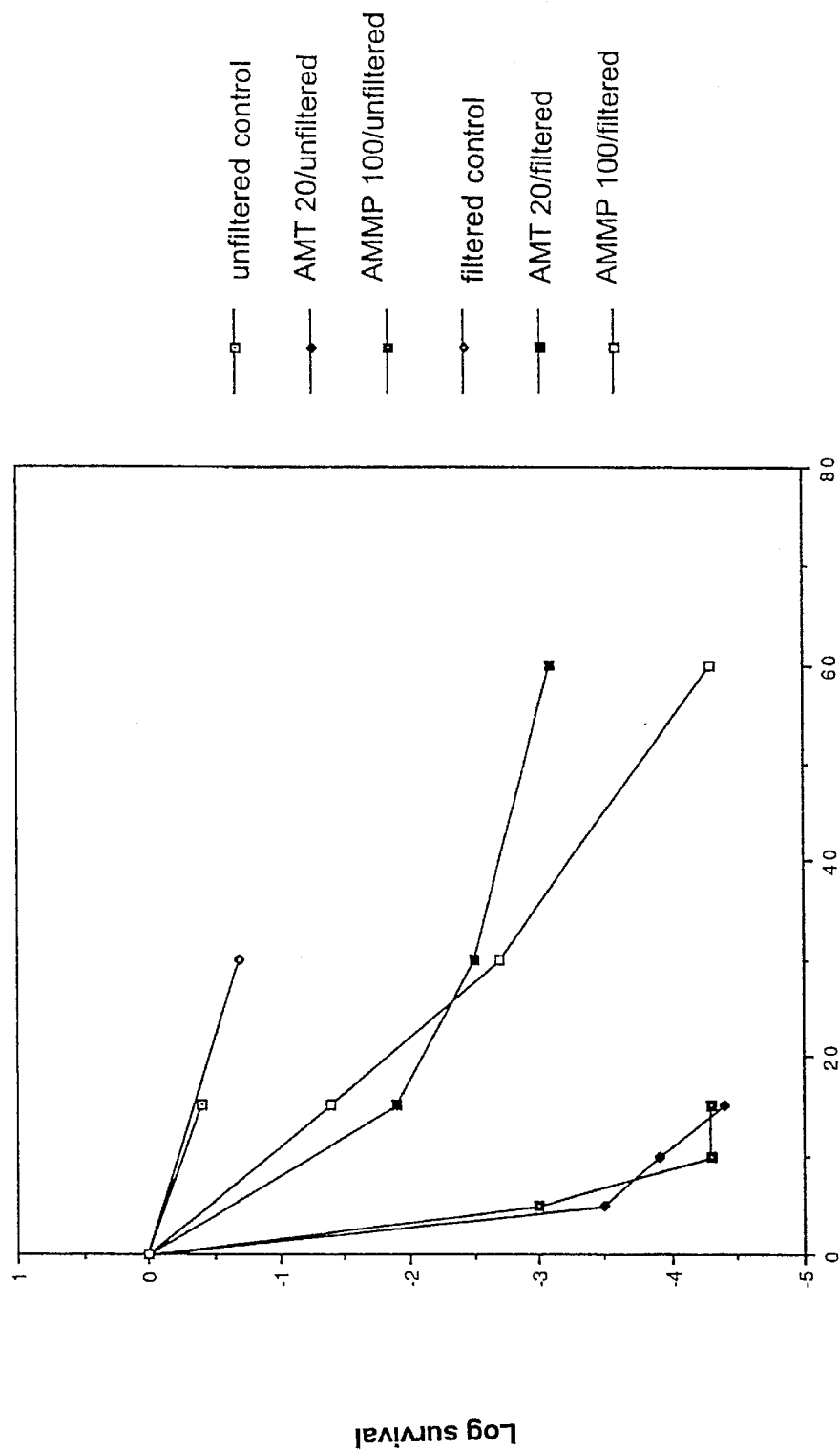
FIG. 32 is a graph showing the viral inactivation of cell-associated HIV in serum by 4'-aminomethyl-4,5',8-trimethylpsoralen (AMT) and 4'-aminomethyl-4,5'-dimethyl-8-methoxypsoralen (AMMP) when irradiated with and without a liquid filter providing Wavelength cutoffs at 320 nm and at 360

The results are shown in Tables 11 and 12, and FIGS. 31 (for samples in media) and 32 (for serum samples). It is clear that the inactivation is still effective when UV is filtered. In the culture media, the sample treated with filtered UV reached total inactivation according to the MT-2 infectivity assay within 2 minutes irradiation. In the serum, AMMP was an effective compound at the concentration used, achieving complete detectible inactivation within 60'.

TABLE 11

SERUM

| SAMPLE | Psoralen | minutes | filter | viral titer | drop in titer |
|---|---|---|---|---|---|
| 1 | 0 | 0 | no | 5.2 | 0 |
| 2 | 0 | 15 | no | 4.8 | −0.4 |
| 3 | AMT 20 | 0 | no | 5.1 | 0 |
| 4 | AMT 20 | 5 | no | 1.6 | −3.5 |
| 5 | AMT 20 | 10 | no | 1.2 | −3.9 |
| 6 | AMT 20 | 15 | no | 0.7 | −4.4 |
| 7 | AMMP 100 | 0 | no | 5.0 | 0 |
| 8 | AMMP 100 | 5 | no | 2.0 | −3.0 |
| 9 | AMMP 100 | 10 | no | <0.7 | >−4.3 |
| 10 | AMMP 100 | 15 | no | <0.7 | >−4.3 |
| 11 | 0 | 60 | yes | 4.5 | −.7 |
| 12 | AMT 20 | 15 | yes | 3.2 | −1.9 |
| 13 | AMT 20 | 30 | yes | 2.6 | −2.5 |
| 14 | AMT 20 | 60 | yes | 2.0 | −3.1 |
| 15 | AMMP 100 | 15 | yes | 3.6 | −1.4 |
| 16 | AMMP 100 | 30 | yes | 2.3 | −2.7 |
| 17 | AMMP 100 | 60 | yes | <0.7 | >−4.3 |

TABLE 12

CULTURE MEDIUM

| SAMPLE | Psoralen | minutes | filter | viral titer | drop in titer |
|---|---|---|---|---|---|
| 1 | 0 | 0 | no | 4.9 | 0 |
| 2 | 0 | 1 | no | 3.9 | −1 |
| 3 | AMT 20 | 0 | no | 4.1 | 0 |
| 4 | AMT 20 | 0.25 | no | <0.7 | >3.4 |
| 5 | AMT 20 | 0.5 | no | <0.7 | >3.4 |
| 6 | AMT 20 | 1 | no | <0.7 | >3.4 |
| 7 | 0 | 4 | yes | 2.9 | −2.0 |
| 8 | AMT 20 | 1 | yes | 1.7 | −2.4 |
| 9 | AMT 20 | 2 | yes | <0.7 | >−3.4 |
| 10 | AMT 20 | 4 | yes | <0.7 | >−3.4 |

EXAMPLE 16

Examples 14 and 15 demonstrated that a reduction in AMT binding with nucleic acid results when the source of irradiation is filtered. This experiment demonstrates that an increase in the concentration of AMT will increase nucleic acid binding to compensate for the drop resulting from the filter.

Pathogen inactivation efficiency as a function of concentration was evaluated for AMT. Various concentrations of AMT were compared for ability to inactivate cell-associated virus (HIV). Inactivation of cell-associated HIV was performed as follows.

HIV-infected H9 cells were seeded into human serum or synthetic media. Aliquots of serum were placed in water jacketed Pyrex chambers, described in Example 10, and treated with AMT at the following concentrations: 0 µg/mL, 20 µg/mL, 40 µg/mL, 80 µg/mL and 160 µg/mL. Aliquots of medium were treated with AMT at concentrations of 0 µg/mL and 20 µg/mL. Serum samples were then treated for 20 minutes with 320–400 nm (20mW/cm$^2$) using the same irradiation device used in Example 10 and the liquid filter solution of $Co(No_3)_2$ and $NiSO_4$ described above, which removes the 365 nm component. Media samples were irradiated for 1 minute. Control containers of serum and of culture media were treated with UVA light alone. Controls for each concentration of AMT were not irradiated. Residual HIV infectivity was assayed using the MT-2 infectivity assay. Hanson, C. V., J. Clin. Micro 28:2030 (1990).

Figure 33:
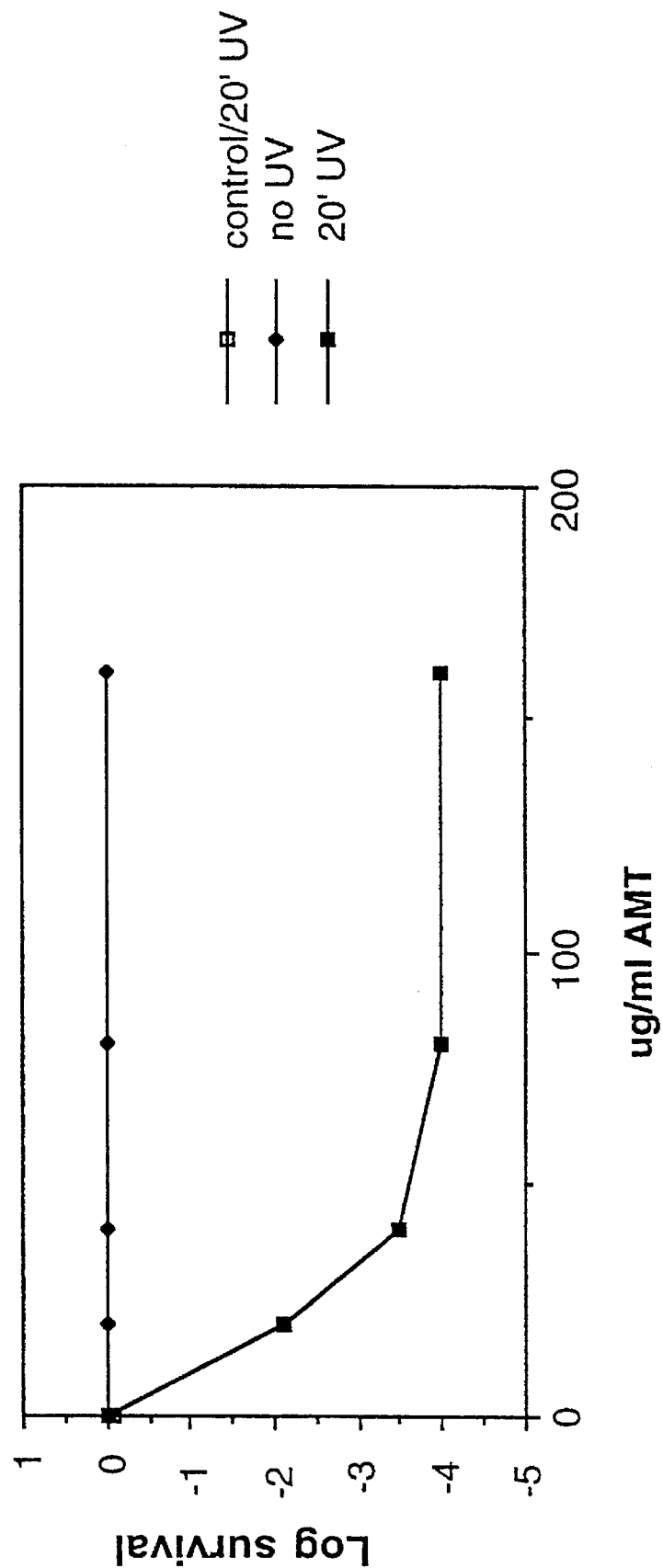
FIG. 33 is a graph showing the photoaddition of 4'-aminomethyl-4,5',8-trimethylpsoralen (AMT) to nucleic acid in serum at varied concentrations of AMT.
Figure 34:
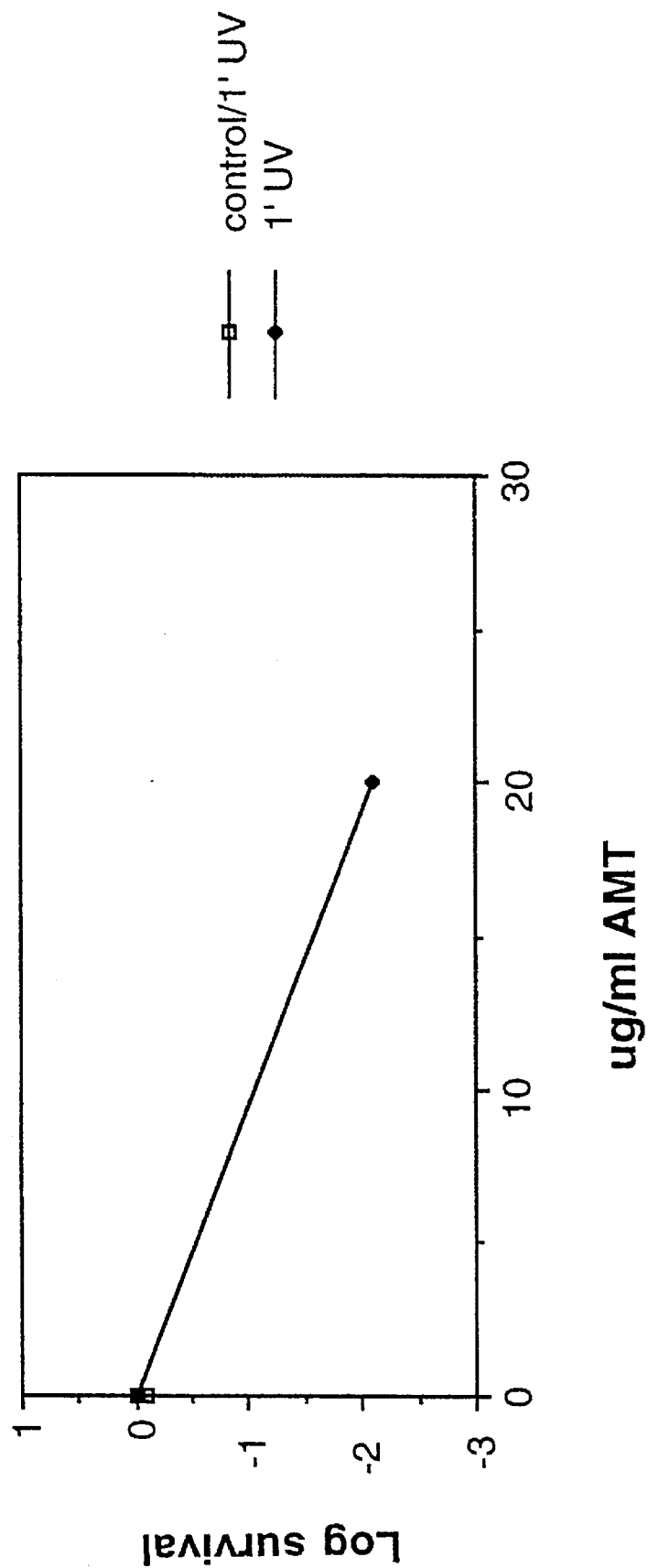
FIG. 34 is a graph showing the photoaddition of 4'-aminomethyl-4,5',8-trimethylpsoralen (AMT) to nucleic acid in medium at varied concentrations of AMT.

The results are shown in Table 13, FIG. 33 (for serum samples) and FIG. 34 (for serum free samples). Clearly, at concentrations of 80 μg/mL or more, AMT effectively inactivated the cell-associated HIV beyond the power of detection of the MT-2 infectivity assay. Thus, increased concentration of AMT compensates for reduced binding as a result of ultraviolet filtering.

TABLE 13

Inactivation of Cell-Free HIV in Serum and Culture Media

| SAMPLE | AMT | filter | viral titer | drop in titer |
|---|---|---|---|---|
| SERUM | | | | |
| 1 | 0 | 0 | 4.6 | 0 |
| 2 | 0 | 20 | 4.5 | -.1 |
| 3 | 20 | 0 | 4.8 | 0 |
| 4 | 40 | 0 | 4.8 | 0 |
| 5 | 80 | 0 | 4.8 | 0 |
| 6 | 160 | 0 | 4.6 | 0 |
| 7 | 20 | 20 | 2.6 | -2.1 |
| 8 | 40 | 20 | 1.2 | -3.5 |
| 9 | 80 | 20 | <0.7 | >-4.0 |
| 10 | 160 | 20 | <0.7 | >-4.0 |
| MEDIA | | | | |
| 11 | 0 | 0 | 4.3 | 0 |
| 12 | 0 | 1 | 4.2 | -.1 |
| 13 | 20 | 0 | 3.8 | 0 |
| 14 | 20 | 1 | 1.7 | -2.1 |

EXAMPLE 17

As shown in Example 13, the damage to bilirubin and uric acid from light alone is controlled by filtering out certain wavelengths. In this example, it is determined whether, in combination, irradiation and photoreactive compounds effect common clinical tests. In this example, AMT and AMMP, both in the presence of ultraviolet light, are compared with regard to their effect on nineteen common clinical chemistry tests. As in Example 13, theorizing that any reduction in Uric Acid and Total Bilirubin might be do to wavelengths other than those needed to activate psoralens, experiments were also performed under conditions to filter out these wavelengths.

As with prior experiments, stored patient serum was used. Two patient samples (both approximately one week old) were selected for testing. One sample appeared to have a low to normal bilirubin upon visual inspection ("Patient 1"). The other appeared to have a normal to high bilirubin level ("Patient 2").

A total sample volume of 0.4 mL was selected for convenience. Both AMT and AMMP were used at high concentration (200 μg/mL). 20 minute irradiations were performed on the HRI-100 device with and without the liquid filter in the sample trough. The irradiations were performed without cooling of the reaction chamber.

The samples were tested i) without any treatment, ii) with UV irradiation only (i.e. no compound), iii) with compound but no light, and iv) with compound and light. The results are shown in Tables 14–19, below. Seventeen of nineteen tests show little or no effect when samples are exposed to a combination of photoreactive compound and ultraviolet light.

Uric acid and bilirubin assay results were reduced when samples were exposed to compound and irradiation. However, this effect can be greatly limited by filtering light that is not necessary to activate the compounds. The effect on uric acid and bilirubin was further reduced where treatment was with AMMP rather than with AMT.

TABLE 14

Patient 1 (no filter)

| Tests | Untreated | AMT Only | AMMP Only | UV Only |
|---|---|---|---|---|
| GLUCOSE | 97 | 97 | 97 | 98 |
| SODIUM | 126 | 128 | 127 | 126 |
| POTASSIUM | 6.8 | 6.9 | 6.9 | 6.8 |
| CHLORIDE | 97 | 98 | 98 | 99 |
| $CO_2$ | 23 | 22 | 22 | 22 |
| BUN | 16 | 16 | 16 | 16 |
| CREAT | 1.5 | 1.7 | 1.6 | 1.6 |
| TOTAL | 4.9 | 5.0 | 4.9 | 5.1 |
| ALBUMIN | 2.7 | 2.6 | 2.6 | 2.7 |
| CALCIUM | 7.8 | 7.7 | 7.8 | 8.1 |
| PHOS ACID | 5.1 | 5.2 | 5.1 | 5.1 |
| URIC ACID | 6.9 | 6.9 | 6.9 | 5.7 |
| BILIRUBIN | 0.3 | 0.3 | 0.3 | 0.1 |
| AMYLASE | <48 | <48 | <48 | <48 |
| ALK PHOS | 94 | 98 | 99 | 91 |
| ALT | 22 | 26 | 25 | 21 |
| AST | 18 | 32 | 30 | 17 |
| LDH | 132 | 119 | 124 | 130 |
| CPK | <25 | <25 | <25 | <25 |

TABLE 15

Patient 1 (no filter)

| Tests | Untreated | AMT/UV | AMMP/UV | UV Only |
|---|---|---|---|---|
| GLUCOSE | 97 | 99 | 98 | 98 |
| SODIUM | 126 | 127 | 127 | 126 |
| POTASSIUM | 6.8 | 6.9 | 6.9 | 6.8 |
| CHLORIDE | 97 | 99 | 99 | 99 |
| $CO_2$ | 23 | 23 | 22 | 22 |
| BUN | 16 | 16 | 16 | 16 |
| CREAT | 1.5 | 1.6 | 1.6 | 1.6 |
| TOTAL | 4.9 | 5.0 | 5.1 | 5.1 |
| ALBUMIN | 2.7 | 2.6 | 2.7 | 2.7 |
| CALCIUM | 7.8 | 7.9 | 7.9 | 8.1 |
| PHOS ACID | 5.1 | 5.2 | 5.2 | 5.1 |
| URIC ACID | 6.9 | 3.6 | 4.6 | 5.7 |
| BILIRUBIN | 0.3 | 0.2 | 0.3 | 0.1 |
| AMYLASE | <48 | <48 | <48 | <48 |
| ALK PHOS | 94 | 93 | 95 | 91 |
| ALT | 22 | 17 | 24 | 21 |
| AST | 18 | 22 | 23 | 17 |
| LDH | 132 | 119 | 122 | 130 |
| CPK | <25 | <25 | <25 | <25 |

TABLE 16

Patient 1 (with liquid filter)

| Tests | Untreated | AMT Only | AMMP Only | UV Only |
|---|---|---|---|---|
| GLUCOSE | 97 | 99 | 99 | 98 |
| SODIUM | 126 | 129 | 129 | 129 |
| POTASSIUM | 6.8 | 6.9 | 7.0 | 6.9 |
| CHLORIDE | 97 | 100 | 100 | 99 |
| $CO_2$ | 23 | 20 | 20 | 20 |
| BUN | 16 | 16 | 16 | 16 |
| CREAT | 1.5 | 1.7 | 1.7 | 1.6 |
| TOTAL | 4.9 | 5.2 | 5.0 | 5.0 |
| ALBUMIN | 2.7 | 2.7 | 2.7 | 2.7 |
| CALCIUM | 7.8 | 7.9 | 8.0 | 8.1 |
| PHOS ACID | 5.1 | 5.2 | 5.2 | 5.2 |
| URIC ACID | 6.9 | 4.6 | 5.6 | 6.9 |
| BILIRUBIN | 0.3 | 0.2 | 0.2 | 0.3 |
| AMYLASE | <48 | <48 | <48 | <48 |
| ALK PHOS | 94 | 97 | 99 | 95 |
| ALT | 22 | 21 | 23 | 20 |
| AST | 18 | 28 | 30 | 21 |

TABLE 16-continued

Patient 1 (with liquid filter)

| Tests | Un-treated | AMT Only | AMMP Only | UV Only |
|---|---|---|---|---|
| LDH | 132 | 122 | 124 | 138 |
| CPK | <25 | <25 | <25 | <25 |

TABLE 17

Patient 2 (no filter)

| Tests | Un-treated | AMT/UV | AMMP/UV | UV Only |
|---|---|---|---|---|
| GLUCOSE | 97 | 98 | 97 | 98 |
| SODIUM | 126 | 128 | 129 | 129 |
| POTASSIUM | 5.0 | 5.0 | 5.1 | 5.1 |
| CHLORIDE | 94 | 94 | 95 | 94 |
| $CO_2$ | 23 | 22 | 22 | 22 |
| BUN | 10 | 11 | 10 | 11 |
| CREAT | 0.9 | 0.9 | 1.0 | 1.1 |
| TOTAL | 6.8 | 6.6 | 6.9 | 7.0 |
| ALBUMIN | 4.2 | 4.2 | 4.2 | 4.2 |
| CALCIUM | 9.6 | 9.3 | 9.5 | 9.8 |
| PHOS ACID | 3.8 | 3.8 | 3.9 | 3.9 |
| URIC ACID | 4.6 | 4.6 | 4.6 | 4.1 |
| BILIRUBIN | 1.0 | 1.0 | 1.0 | 0.6 |
| AMYLASE | 136 | 135 | 137 | 138 |
| ALK PHOS | 86 | 89 | 90 | 86 |
| ALT | 30 | 29 | 33 | 28 |
| AST | 29 | 32 | 36 | 31 |
| LDH | 119 | 108 | 113 | 118 |
| CPK | 26 | 27 | 26 | <25 |

TABLE 18

Patient 2 (no filter)

| Tests | Un-treated | AMT/UV | AMMP/UV | UV Only |
|---|---|---|---|---|
| GLUCOSE | 97 | 99 | ND | 98 |
| SODIUM | 126 | 128 | ND | 129 |
| POTASSIUM | 5.0 | 5.1 | ND | 5.1 |
| CHLORIDE | 94 | 96 | ND | 94 |
| $CO_2$ | 23 | 21 | ND | 22 |
| BUN | 10 | 10 | ND | 11 |
| CREAT | 0.9 | 0.9 | ND | 1.1 |
| TOTAL | 6.8 | 6.8 | ND | 7.0 |
| ALBUMIN | 4.2 | 4.1 | ND | 4.2 |
| CALCIUM | 9.6 | 9.6 | ND | 9.8 |
| PHOS ACID | 3.8 | 3.9 | ND | 3.9 |
| URIC ACID | 4.6 | 2.2 | ND | 4.1 |
| BILIRUBIN | 1.0 | 0.6 | ND | 0.6 |
| AMYLASE | 136 | 135 | ND | 138 |
| ALK PHOS | 86 | 89 | ND | 86 |
| ALT | 30 | 27 | ND | 28 |
| AST | 29 | 28 | ND | 31 |
| LDH | 119 | 112 | ND | 118 |
| CPK | 26 | <25 | ND | <25 |

TABLE 19

Patient 2 (with liquid filter)

| Tests | Un-treated | AMT/UV | AMMP/UV | UV Only |
|---|---|---|---|---|
| GLUCOSE | 97 | 99 | 99 | 99 |
| SODIUM | 126 | 130 | 129 | 127 |
| POTASSIUM | 5.0 | 5.1 | 5.1 | 5.1 |
| CHLORIDE | 94 | 96 | 96 | 96 |
| $CO_2$ | 23 | 21 | 22 | 22 |

TABLE 19-continued

Patient 2 (with liquid filter)

| Tests | Un-treated | AMT/UV | AMMP/UV | UV Only |
|---|---|---|---|---|
| BUN | 10 | 10 | 10 | 10 |
| CREAT | 0.9 | 1.0 | 1.0 | 0.9 |
| TOTAL | 6.8 | 6.8 | 6.8 | 6.8 |
| ALBUMIN | 4.2 | 4.3 | 4.2 | 4.2 |
| CALCIUM | 9.6 | 9.6 | 9.7 | 9.7 |
| PHOS ACID | 3.8 | 4.0 | 4.0 | 3.9 |
| URIC ACID | 4.6 | 3.3 | 3.9 | 4.6 |
| BILIRUBIN | 1.0 | 0.8 | 0.9 | 1.0 |
| AMYLASE | 136 | 128 | 137 | 139 |
| ALK PHOS | 86 | 89 | 90 | 87 |
| ALT | 30 | 29 | 32 | 32 |
| AST | 29 | 39 | 36 | 30 |
| LDH | 119 | 113 | 113 | 119 |
| CPK | 26 | <25 | <25 | 26 |

EXAMPLE 18

Example 17 shows that AMMP is much less destructive than either AMT or 8-MOP. Without intending to be limited to any mechanism, it is postulated that the reduction of bilirubin and uric acid assay values result from oxygen radicals produced by photoreactive compounds during and after irradiation. To determine the generation of active oxygen species by AMMP relative to 8-MOP and AMT, the production of superoxide radical was measured.

Solutions (100 ul) containing the psoralen compound (0.14 mM), nitro blue tetrazolium (0.16 mM), and potassium phosphate (0.05M, pH 7.9) were irradiated on the HRI-100 device with UV light in the range of 320–400 nm (20 mW/cm$^2$) at 25° C. for the indicated times. Following irradiation, the samples were loaded on a microtiter plate and the absorbance at 490 nm determined. nitro blue tetrazolium without psoralen was also irradiated as a control.

Figure 35:
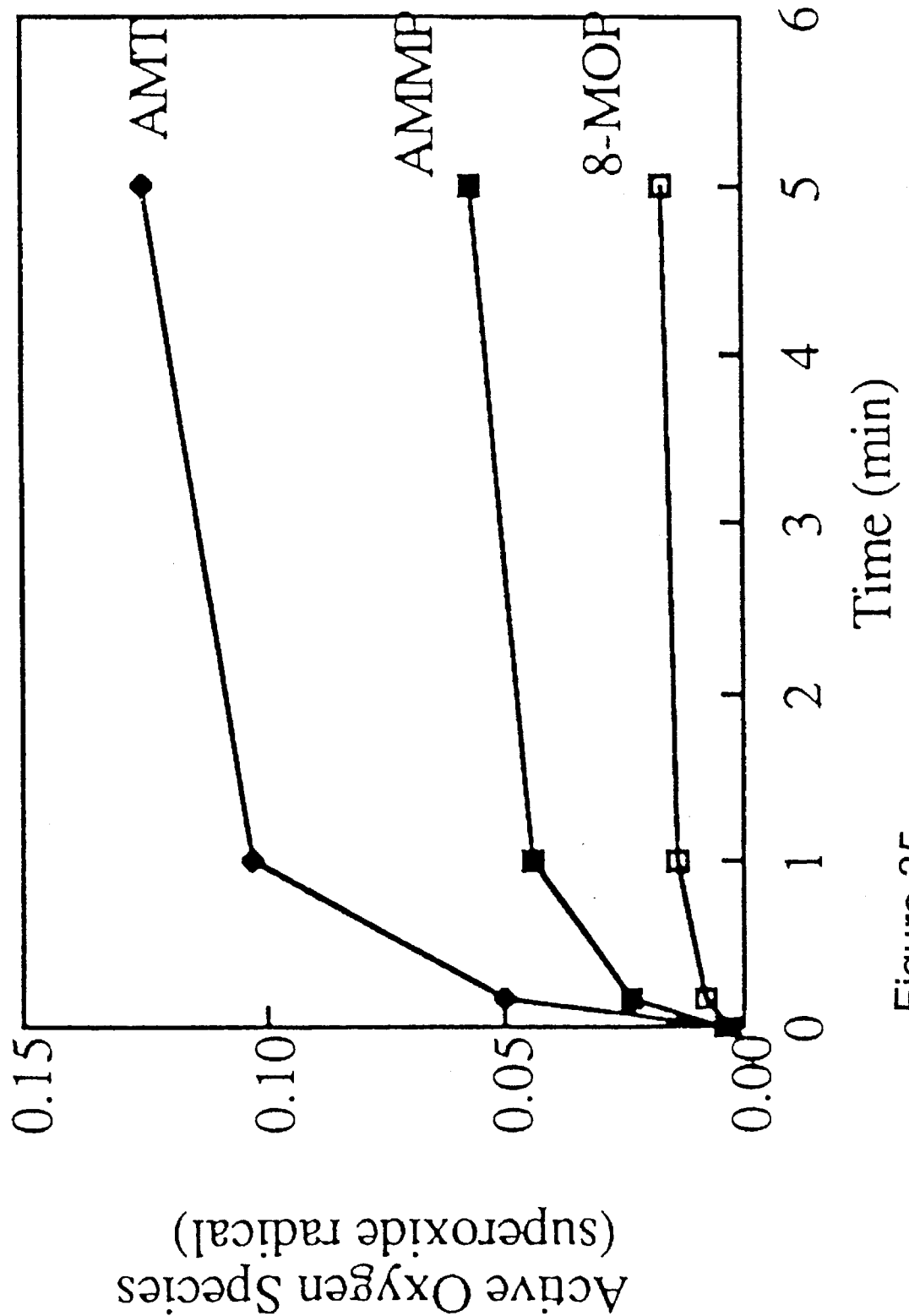
FIG. 35 is a graph showing the production of active oxygen species by 4'-aminomethyl-4,5',8-trimethylpsoralen (AMT), 4'-aminomethyl-4,5'-dimethyl-8-methoxypsoralen (AMMP) and 8-methoxypsoralen (8-MOP) over time.

The results show that AMMP produced significantly less superoxide radical than AMT (FIG. 35). This supports the above postulation that oxygen radicals produced by some photoreactive compounds during and after irradiation cause damage to some clinical analytes, such as bilirubin and uric acid, making them less compatible with chemistry tests. On the other hand, AMMP, which produced less oxygen radicals during and after irradiation, may be more compatible with chemistry tests.

EXAMPLE 19

In the previous examples, the compatibility of the present invention with chemistry tests was examined. This example examines whether the methods of the present invention have adverse effects upon antibody based clinical tests. This experiment looks at the effects of AMMP and ultraviolet light on a clinical Rubella IgG antibody assay.

As with prior experiments, stored patient serum was used. One patient sample (stored for several weeks) was selected for testing.

A total sample volume of 1 mL was selected for convenience. AMMP was added to a concentration of 90 μg/mL. Irradiations were performed for 10, 20, or 30 minutes on the Device of Example 2. The irradiations were performed without cooling of the reaction chamber.

The serum was treated as follows: i) no treatment, ii) compound but no light, and iii) compound and varied times of irradiation. The serum was then tested for the presence of Rubella IgG by SmithKline Beecham Laboratories, California, using an enzyme linked immunosorbant assay. Rubella antigen was attached to a solid phase surface such as wells in a plastic strip. The Rubella antigen, if present in the serum, bound to the attached antigen. Unbound antibody was then removed by washing. An enzyme conjugate anti-human IgG was added which binds to the antigen-antibody complex. Unbound conjugate was then removed by washing. Next, enzyme substrate was added and hydrolyzed by bound enzyme conjugate. Finally, after a certain amount of time, the reaction was stopped by the addition of sodium phosphate. The resulting complex was analyzed on a Witaker EIA machine, Witaker, Inc.

The results are shown in Table 20, below. The results demonstrate that the antibody assay is uneffected when samples are exposed to a combination of AMMP and less than 30 minutes ultraviolet light. The only discernable drop in Rubella IgG antibody occurred when the sample was irradiated for 30 minutes (Sample E, Table 20). This reduction in antibody detection may be attributable to warming of the sample during irradiation. Such levels of heat can denature antibodies. It is likely that even the small drop in antibody detected in sample E may be prevented by cooling the sample chamber of the photoactivation device during irradiation.

TABLE 20

| SAMPLE | AMMP | UV | RUBELLA IgG |
|---|---|---|---|
| A | None | None | 2.18 |
| B | 90 μg/ml | None | 2.35 |
| C | 90 μg/ml | 10 min. | 2.00 |
| D | 90 μg/ml | 20 min. | 2.06 |
| E | 90 μg/ml | 30 min. | 1.82 |

From the above it should be evident that the present invention provides methods for inactivation of contaminants in material intended for in vitro use, and in particular the inactivation of pathogens in human fluids prior to clinical testing. The methods are effective against a wide range of pathogens. Furthermore, the methods do not unduly interfere with laboratory operations or clinical analysis.

We claim:

1. A complex, comprising the compound having the formula:

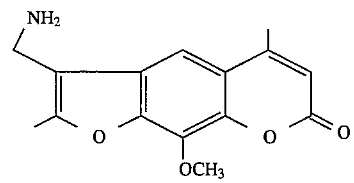

or a salt thereof, coupled to nucleic acid.

2. A complex as in claim 1 wherein said coupling is covalent.

3. A complex as in claim 1 wherein said nucleic acid is selected from the group consisting of viral, bacterial, fungal, mycoplasmal and protozoan nucleic acid.

4. A complex as in claim 1 wherein said nucleic acid is DNA.

5. A complex as in claim 1 wherein said nucleic acid is RNA.

6. A method of producing a 4'-aminomethyl-4,5'-dimethyl-8-methoxypsoralen: nucleic acid complex, comprising the steps:

a) adding 4'-aminomethyl-4,5'-dimethyl-8-methoxypsoralen to nucleic acid; and binding said 4'-aminomethyl-4,5'-dimethyl-8-methoxypsoralen to said nucleic acid.

* * * * *